(12) United States Patent
Roth et al.

(10) Patent No.: US 8,100,963 B2
(45) Date of Patent: *Jan. 24, 2012

(54) BIODEGRADABLE DEVICE

(75) Inventors: Noah M. Roth, Highland Park, NJ (US);
Kishore Kondabatni, Atlanta, GA (US);
Chandana Karnati, Atlanta, GA (US);
William Brodbeck, Hudson, OH (US)

(73) Assignee: Icon Medical Corp., Cleveland, OH (US)

(\*) Notice: Subject to any disclaimer, the term of this patent is extended or adjusted under 35 U.S.C. 154(b) by 486 days.

This patent is subject to a terminal disclaimer.

(21) Appl. No.: 11/646,890

(22) Filed: Dec. 28, 2006

(65) Prior Publication Data

US 2007/0123973 A1 May 31, 2007

Related U.S. Application Data

(63) Continuation-in-part of application No. 10/209,591, filed on Jul. 31, 2002, now abandoned, which is a continuation-in-part of application No. 10/039,816, filed on Oct. 26, 2001, now abandoned, application No. 11/646,890, which is a continuation-in-part of application No. 11/283,434, filed on Nov. 18, 2005, now Pat. No. 8,070,796, application No. 11/646,890, which is a continuation-in-part of application No. 11/283,330, filed on Nov. 18, 2005, now Pat. No. 7,967,855, application No. 11/646,890, which is a continuation-in-part of application No. 11/337,225, filed on Jan. 20, 2006, which is a continuation-in-part of application No. 10/209,591, which is a continuation-in-part of application No. 10/039,816, application No. 11/646,890, which is a continuation-in-part of application No. 11/283,434.

(60) Provisional application No. 60/629,397, filed on Nov. 19, 2004, provisional application No. 60/658,411, filed on Mar. 3, 2005, provisional application No. 60/629,470, filed on Nov. 19, 2004, provisional application No. 60/658,374, filed on Mar. 3, 2005.

(51) Int. Cl.
*A61F 2/06* (2006.01)
*A61M 29/00* (2006.01)
(52) U.S. Cl. ............... 623/1.42; 606/198; 623/1.15
(58) Field of Classification Search .............. 623/1.15, 623/1.42, 1.46; 606/191, 194, 195, 198
See application file for complete search history.

(56) References Cited

U.S. PATENT DOCUMENTS 3,964,482 A   6/1976   Gerstel
(Continued)

FOREIGN PATENT DOCUMENTS

EP            04330011 A1   6/1991
(Continued)

OTHER PUBLICATIONS

Microsystems for Drug and Gene Deliver, Michael L. Reed, Senior Member, IEEE and Whye-Kei Lye, Member, IEEE. Proceedings of the IEEE, vol. 92 No. 1, Jan. 2004.
(Continued)

*Primary Examiner* — Vy Bui
(74) *Attorney, Agent, or Firm* — Fay Sharpe LLP; Brian E. Turung

(57) ABSTRACT

A device that is at least partially formed of a biodegradable polymer. The device can be at least partially formed by MEMS technology. The device can include one or more micro-structures that are also formed by MEMS technology. The device can include one or more agents that can be controllably and/or uncontrollably released from the device.

25 Claims, 7 Drawing Sheets

U.S. PATENT DOCUMENTS

| | | | |
|---|---|---|---|
| 4,733,665 A | 3/1988 | Palmaz | |
| 4,739,762 A | 4/1988 | Palmaz | |
| 4,773,665 A | 9/1988 | Hindle | |
| 4,776,337 A | 10/1988 | Palmaz | |
| 4,888,389 A | 12/1989 | Kennedy et al. | |
| 4,942,204 A | 7/1990 | Kennedy | |
| 5,024,671 A | 6/1991 | Tu et al. | |
| 5,037,392 A | 8/1991 | Hillstead | |
| 5,051,272 A | 9/1991 | Hermes et al. | |
| 5,059,166 A | 10/1991 | Fischell et al. | |
| 5,067,491 A | 11/1991 | Taylor, II et al. | |
| 5,073,381 A | 12/1991 | Ivan et al. | |
| 5,102,417 A | 4/1992 | Palmaz | |
| 5,108,424 A | 4/1992 | Hoffman, Jr. et al. | |
| 5,116,318 A | 5/1992 | Hillstead | |
| 5,180,366 A | 1/1993 | Woods | |
| 5,185,408 A | 2/1993 | Tang et al. | |
| 5,195,984 A | 3/1993 | Schatz | |
| 5,197,977 A | 3/1993 | Hoffman, Jr. et al. | |
| 5,246,452 A | 9/1993 | Sinnott | |
| 5,283,257 A | 2/1994 | Gregory | |
| 5,304,121 A | 4/1994 | Sahatjian | |
| 5,306,250 A | 4/1994 | March et al. | |
| 5,316,023 A | 5/1994 | Palmaz | |
| 5,344,426 A | 9/1994 | Lau | |
| 5,370,681 A | 12/1994 | Herweck | |
| 5,383,927 A | 1/1995 | Degoicoechea et al. | |
| 5,383,928 A | 1/1995 | Scott et al. | |
| 5,417,981 A | 5/1995 | Endo | |
| 5,443,498 A | 8/1995 | Fontaine | |
| 5,449,382 A | 9/1995 | Dayton | |
| 5,464,650 A | 11/1995 | Berg et al. | |
| 5,500,013 A | 3/1996 | Buscemi et al. | |
| 5,516,781 A | 5/1996 | Morris et al. | |
| 5,545,208 A | 8/1996 | Wolff et al. | |
| 5,556,754 A | 9/1996 | Singer | |
| 5,563,056 A | 10/1996 | Swan et al. | |
| 5,563,146 A | 10/1996 | Morris et al. | |
| 5,571,170 A | 11/1996 | Palmaz | |
| 5,578,075 A | 11/1996 | Dayton | |
| 5,578,645 A | 11/1996 | Askanazi | |
| 5,605,696 A | 2/1997 | Eury et al. | |
| 5,609,629 A | 3/1997 | Fearnot et al. | |
| 5,616,608 A | 4/1997 | Kinsella et al. | |
| 5,624,411 A | 4/1997 | Tuch | |
| 5,649,977 A | 7/1997 | Campbell | |
| 5,665,728 A | 9/1997 | Morris et al. | |
| 5,679,400 A | 10/1997 | Tuch | |
| 5,695,516 A | 12/1997 | Fischell et al. | |
| 5,716,981 A | 2/1998 | Hunter et al. | |
| 5,725,572 A | 3/1998 | Lam et al. | |
| 5,733,303 A | 3/1998 | Israel et al. | |
| 5,733,925 A | 3/1998 | Kunz et al. | |
| 5,735,871 A | 4/1998 | Sgro | |
| 5,755,781 A | 5/1998 | Jayaraman | |
| 5,772,864 A | 6/1998 | M.o slashed.ller et al. | |
| 5,776,183 A | 7/1998 | Kanesaka et al. | |
| 5,807,944 A | 9/1998 | Hirt et al. | |
| 5,811,447 A | 9/1998 | Kunz | |
| 5,824,045 A | 10/1998 | Alt | |
| 5,824,049 A | 10/1998 | Ragheb et al. | |
| 5,824,077 A | 10/1998 | Mayer | |
| 5,837,313 A | 11/1998 | Ding | |
| 5,843,172 A | 12/1998 | Yan | |
| 5,849,368 A | 12/1998 | Hostettler et al. | |
| 5,853,419 A | 12/1998 | Imran | |
| 5,861,027 A | 1/1999 | Trapp | |
| 5,873,904 A | 2/1999 | Ragheb | |
| 5,879,370 A | 3/1999 | Fischell et al. | |
| 5,911,732 A | 6/1999 | Hojeibane | |
| 5,916,585 A | 6/1999 | Cook et al. | |
| 5,962,620 A | 10/1999 | Reich et al. | |
| 5,964,798 A | 10/1999 | Imran | |
| 5,968,091 A | 10/1999 | Pinchuk et al. | |
| 5,981,568 A | 11/1999 | Kunz et al. | |
| 5,993,972 A | 11/1999 | Reich et al. | |
| 6,007,573 A | 12/1999 | Wallace et al. | |
| 6,059,810 A | 5/2000 | Brown et al. | |
| 6,066,325 A | 5/2000 | Wallace | |
| 6,074,659 A | 6/2000 | Kunz | |
| 6,093,520 A | 7/2000 | Vladimirsky | |
| 6,096,070 A | 8/2000 | Ragheb | |
| 6,099,561 A | 8/2000 | Alt | |
| 6,120,536 A | 9/2000 | Ding et al. | |
| 6,120,847 A | 9/2000 | Yang | |
| 6,146,358 A | 11/2000 | Rowe | |
| 6,156,062 A | 12/2000 | McGuinness | |
| 6,156,373 A | 12/2000 | Zhang | |
| 6,162,247 A | 12/2000 | Weadock et al. | |
| 6,171,609 B1 | 1/2001 | Kunz | |
| 6,197,013 B1 * | 3/2001 | Reed et al. | 604/509 |
| 6,200,337 B1 | 3/2001 | Moriuchi et al. | |
| 6,200,589 B1 | 3/2001 | Kennedy et al. | |
| 6,200,960 B1 | 3/2001 | Khachigan | |
| 6,206,916 B1 | 3/2001 | Furst | |
| 6,221,099 B1 | 4/2001 | Andersen et al. | |
| 6,245,537 B1 | 6/2001 | Williams | |
| 6,258,121 B1 | 7/2001 | Yang et al. | |
| 6,268,390 B1 | 7/2001 | Kunz | |
| 6,273,908 B1 | 8/2001 | Ndondo-Lay | |
| 6,273,913 B1 | 8/2001 | Wright | |
| 6,287,628 B1 | 9/2001 | Hossainy | |
| 6,290,721 B1 | 9/2001 | Heath | |
| 6,299,604 B1 | 10/2001 | Ragheb et al. | |
| 6,306,421 B1 | 10/2001 | Kunz | |
| 6,322,847 B1 | 11/2001 | Zhang | |
| 6,334,856 B1 | 1/2002 | Allen | |
| 6,335,029 B1 | 1/2002 | Kamath et al. | |
| 6,346,133 B1 | 2/2002 | Narasimhan | |
| 6,356,600 B1 | 3/2002 | Kirsteins | |
| 6,358,268 B1 | 3/2002 | Hunt et al. | |
| 6,358,556 B1 | 3/2002 | Ding et al. | |
| 6,358,989 B1 | 3/2002 | Kunz | |
| 6,365,171 B1 | 4/2002 | Kennedy et al. | |
| 6,365,616 B1 | 4/2002 | Kohn | |
| 6,368,658 B1 | 4/2002 | Schwarz et al. | |
| 6,369,065 B1 | 4/2002 | Chatelain | |
| 6,379,379 B1 | 4/2002 | Wang | |
| 6,379,381 B1 | 4/2002 | Hossainy | |
| 6,391,052 B2 | 5/2002 | Buirge et al. | |
| 6,398,863 B1 | 6/2002 | Okinaka et al. | |
| 6,399,144 B2 | 6/2002 | Dinh et al. | |
| 6,419,692 B1 | 7/2002 | Yang et al. | |
| 6,436,133 B1 | 8/2002 | Furst et al. | |
| 6,440,460 B1 | 8/2002 | Gurny | |
| 6,485,502 B2 | 11/2002 | Don Michael | |
| 6,488,702 B1 | 12/2002 | Besselink | |
| 6,491,938 B2 | 12/2002 | Kunz | |
| 6,515,009 B1 * | 2/2003 | Kunz et al. | 514/411 |
| 6,517,571 B1 | 2/2003 | Brauker et al. | |
| 6,527,802 B1 | 3/2003 | Mayer | |
| 6,528,584 B2 | 3/2003 | Kennedy et al. | |
| 6,530,951 B1 | 3/2003 | Bates | |
| 6,533,949 B1 | 3/2003 | Yeshurun | |
| 6,545,097 B2 | 4/2003 | Pinchuk | |
| 6,555,157 B1 | 4/2003 | Hossainy | |
| 6,555,619 B1 | 4/2003 | Kennedy et al. | |
| 6,558,361 B1 | 5/2003 | Yeshurun | |
| 6,569,195 B2 | 5/2003 | Yang | |
| 6,569,441 B2 | 5/2003 | Kunz | |
| 6,583,251 B1 | 6/2003 | Chaikof et al. | |
| 6,585,764 B2 | 7/2003 | Wright | |
| 6,599,275 B1 | 7/2003 | Fischer | |
| 6,599,928 B2 | 7/2003 | Kunz | |
| 6,607,598 B2 | 8/2003 | Schwarz | |
| 6,623,521 B2 | 9/2003 | Steinke | |
| 6,624,138 B1 | 9/2003 | Sung | |
| 6,641,611 B2 | 11/2003 | Jayaraman | |
| 6,652,575 B2 | 11/2003 | Wang | |
| 6,656,506 B1 | 12/2003 | Wu | |
| 6,656,966 B2 | 12/2003 | Garvey | |
| 6,663,881 B2 | 12/2003 | Kunz | |
| 6,669,502 B1 | 12/2003 | Bernhart | |
| 6,669,718 B2 | 12/2003 | Besselink | |
| 6,676,937 B1 * | 1/2004 | Isner et al. | 424/93.7 |
| 6,695,833 B1 | 2/2004 | Frantzen | |
| 6,709,379 B1 | 3/2004 | Brandau | |

| | | |
|---|---|---|
| 6,720,350 B2 | 4/2004 | Kunz |
| 6,723,120 B2 | 4/2004 | Yan |
| 6,726,923 B2 | 4/2004 | Lyer et al. |
| 6,730,064 B2 | 5/2004 | Ragheb |
| 6,730,349 B2 | 5/2004 | Schwarz |
| 6,730,699 B2 | 5/2004 | Li et al. |
| 6,734,194 B2 | 5/2004 | End et al. |
| 6,743,805 B2 | 6/2004 | End et al. |
| 6,749,554 B1 | 6/2004 | Snow |
| 6,753,071 B1 | 6/2004 | Pacetti |
| 6,759,431 B2 | 7/2004 | Hunter |
| 6,764,505 B1 | 7/2004 | Hossainy |
| 6,770,729 B2 | 8/2004 | Van Antwerp |
| 6,774,278 B1 | 8/2004 | Ragheb |
| 6,780,849 B2 | 8/2004 | Hermann |
| 6,783,793 B1 | 8/2004 | Hossainy |
| 6,790,218 B2 | 9/2004 | Jayaraman |
| 6,790,372 B2 | 9/2004 | Roy |
| 6,808,536 B2 | 10/2004 | Wright |
| 6,861,406 B2 | 3/2005 | Mascarenhas |
| 6,887,851 B2 | 5/2005 | Mascarenhas |
| 6,914,049 B2 | 7/2005 | Mascarenhas |
| 6,924,087 B2 | 8/2005 | Yeshurun |
| 2001/0014717 A1 | 8/2001 | Hossainy et al. |
| 2002/0004101 A1 | 1/2002 | Ding |
| 2002/0013275 A1 | 1/2002 | Kunz |
| 2002/0032414 A1 | 3/2002 | Ragheb et al. |
| 2002/0051730 A1 | 5/2002 | Bodnar et al. |
| 2002/0054900 A1 | 5/2002 | Kamath et al. |
| 2002/0071902 A1 | 6/2002 | Ding |
| 2002/0082679 A1* | 6/2002 | Sirhan et al. ............ 623/1.15 |
| 2002/0091433 A1 | 7/2002 | Ding |
| 2002/0095133 A1 | 7/2002 | Gillis et al. |
| 2002/0142974 A1 | 10/2002 | Kohn |
| 2002/0155737 A1 | 10/2002 | Roy |
| 2003/0026840 A1 | 2/2003 | Plank |
| 2003/0028243 A1 | 2/2003 | Bates |
| 2003/0028244 A1 | 2/2003 | Bates |
| 2003/0036794 A1 | 2/2003 | Ragheb |
| 2003/0040790 A1 | 2/2003 | Furst |
| 2003/0064098 A1 | 4/2003 | Kararliet et al. |
| 2003/0068355 A1 | 4/2003 | Shanley et al. |
| 2003/0083646 A1 | 5/2003 | Sirhan et al. |
| 2003/0093141 A1 | 5/2003 | DiMatteo et al. |
| 2003/0099712 A1 | 5/2003 | Jayaraman |
| 2003/0100499 A1 | 5/2003 | Epstein |
| 2003/0199969 A1 | 10/2003 | Steinke et al. |
| 2003/0216534 A1 | 11/2003 | Chaikof et al. |
| 2003/0228364 A1 | 12/2003 | Nathan |
| 2003/0229390 A1 | 12/2003 | Ashton |
| 2003/0229392 A1 | 12/2003 | Wong |
| 2003/0229393 A1 | 12/2003 | Kutryk et al. |
| 2004/0047909 A1 | 3/2004 | Ragheb |
| 2004/0049265 A1 | 3/2004 | Ding |
| 2004/0072105 A1 | 4/2004 | Yeshurun |
| 2004/0093076 A1 | 5/2004 | White |
| 2004/0093077 A1 | 5/2004 | White |
| 2004/0098014 A1 | 5/2004 | Flugelman |
| 2004/0193247 A1 | 9/2004 | Besselink |
| 2004/0208985 A1 | 10/2004 | Rowen |
| 2004/0219223 A1 | 11/2004 | Kunz |
| 2004/0243225 A1 | 12/2004 | Ragheb |
| 2005/0029223 A1 | 2/2005 | Yeshurun |
| 2005/0165358 A1 | 7/2005 | Yeshurun |
| 2005/0209566 A1 | 9/2005 | Yeshurun |
| 2005/0271701 A1 | 12/2005 | Cottone et al. |
| 2006/0051404 A1 | 3/2006 | Yeshurun |

FOREIGN PATENT DOCUMENTS

| | | |
|---|---|---|
| EP | 0 836839 A2 | 4/1998 |
| EP | 1604697 | 12/2005 |
| WO | WO 93/16176 | 8/1993 |
| WO | WO 94/07529 | 4/1994 |
| WO | WO 99/18998 | 4/1999 |
| WO | WO 99/49907 | 10/1999 |
| WO | WO 99/56663 | 11/1999 |
| WO | WO 00/12175 | 3/2000 |
| WO | WO 00/41649 | 7/2000 |
| WO | WO 01/17577 | 3/2001 |
| WO | WO 01/45763 | 6/2001 |
| WO | WO 01/97964 | 12/2001 |
| WO | WO 2006/110197 | 10/2006 |

OTHER PUBLICATIONS

*Trapidil Inhibits Monocyte Chemoattractant Protein-1 and macrophage Accumulation After Balloon Arterial Injury in Rabbits*, Poon M, Cohen J, Siddiqui Z, et al., Lab Invest. 1999; 79:1369-1375.

*The TRAPIST study—A multicentre randomized placebo controlled clinical trial of trapidil for prevention of restenosis after coronary stenting, measured by 3-D intravascular ultrasound*, P.W. Serruys, D.P. Foley, M. Pieper, J.A. de Feyter on behalf of the TRAPIST investigators, European Heart Journal (2001) 22, 1938-1947, doi:10.1053/euhj.2001.2627, available online at http://www.idealibrary.com.

Abstract of *Fast and Reproducible Vascular Neointima Formation in the Hamster Carotid Artery: Effects of Trapidil and Captopril*, Matsuno H, Stassen JM, Hoylaerts MF, Verrnylen J, Deckmyn H., Thromb Haemost. Dec. 1995;74(6):1591-6.

*Results of a Meta-Analysis of Trapidil, a PDGF Inhibitor A' A Sufficient Reason for a Second Look to the Pharmacological Approach to Restenosis*, Serruys PW, Banz K, Darcis T, Mignot-A, van Es GA, Schwicker D., J Invasive Cardiol. Oct. 1997;9(8):505512.

*Management of restenosis after Coronary Intervention*, Dangas G, Fuster V., Am Heart J. Aug. 1996:132(2 Pt 1):428-36.

*-New Aspects in Antithrombotic Therapy—Platelet Inhibitors-*, Terres W, Meinertz T., Herz. Feb. 1996:21(1):1-11.

*A Randomized Comparison of Trapidil (triazolopyrimidine), a Platelet-Derived Growth Factor Antagonist Versus Asprin in Prevention of Angiographic Restenosis after Coronary Artery Palmaz-Schatz Stent Implantation*, Galassi AR, Tamburino C, Nicosia A, Russo G, Grassi R, Monaco A, Giuffrida G., Catheter Cardiovasc Interv. Feb. 1999;46(2):162-8.

*Reference Chart Derived From Post-Stent-Implantation Intravascular Ultrasound Predictors of 6-Month Expected Restenosis on Quantitative Coronary Angiography*, P. J. de Feyter, P. Kay, C. Disco, and P. W. Serruys, Circulation, Oct. 1999: 100: 1777-1783.

Abstract of *Trapidil in Preventing Restenosis After Balloon Angioplasty in the Ather Osclerotic Rabbit*, MW Liu, GS Roubin, KA Robinson, AJ Black, JA Hearn, RJ Siegel, and SB King, 3d Circulation 1990 81: 1089-1093.

Abstract of *Effects of Trapidil (Triazolopyrimidine), a Platelet-Derived Growth Factor Antagonist, in Preventing Restenosis After Percutaneous Transluminal Coronary Angioplasty*, Okamoto S, Inden M, Setsuda M, Konishi T, Nakano T, Am Heart J. Jun. 1992; 123(6):1439-44.

Abstract of *Trapidil (triazolopyrimidine), A Platelet-Derived Growth Factor Antagonist, Reduces Restenosis After Percutaneous Transluminal Coronary Angioplasty. Results of the Randomized, Double-Blind STARC Study. Studio Trapidil Versus Aspirin Nella Restenosi Coronarica*, A Maresta, M Balducelli, L Cantini, A Casari, R Chioin, M Fabbri, A Fontanelli, PA Monici Preti, S Repetto, and S De Serv, Circulation, Dec 1994; 90: 2710-2715.

Abstract of *The Trapidil Restenosis Trial (STARC study): Background, Methods and Clinical Characteristics of the Patient Population*. Maresta A, Balducelli M, Cantini L, Casari A, Chioin R, Fontanelli A, Monici Preti PA, Repetto S, Raffaghello S.,Clin Trials Metaanal. Apr. 1994,29(1):31-40.

Abstract of *Pharmacological Properties of Trapidil: Comparison with Other Coronary Vasodilators*, Ohnishi H. Kosuzume H, Yamaguchi K, Sato M, Umehara S, Funato H, Itoh C, Suzuki K, Kitamura Y, Suzuki Y,Itoh R., Nippon Yakurigaku Zasshi. Sep. 1980; 76(6):495-503.

Abstract of *Effects of Trapidil on Thromboxane A2-induced Aggregation of Platelets, Ischemic Changes in Heart and Biosynthesis of Thromboxane A2*, Ohnishi H, Kosuzume H, Hayashi Y, Yamaguchi K, Suzuki Y, Itoh R., Prostaglandins Med. Mar. 1981;6(3):269-81.

Abstract of *Antithrombotic Activity and the Mechanism of Action of Trapidil (Rocomal)*, Suzuki Y, Yamaguchi K, Shimada S, Kitamura Y, Ohnishi H., Prostaglandins Leukot Med. Dec. 1982;9(6):685-95.

Abstract of *Suppression of Fibroblast Proliferation in Vitro and of Myointimal Hyperplasia in Vivo by the Triazolopyrimidine, Trapidil*, Tiell ML, Sussman II, Gordon PB, Saunders RN, Artery. 1983;12(1):33-50.

*Influence of Cardiovascular Drugs on Platelet Aggregation*, Forster W, Block HU, Giessler C. Heinroth I, Mentz P, Ponicke K, Rettkowski W, Zehl U., :Adv Myocardiol. 1983;4:539-47.

*Trapidil in Preventing Restenosis After Balloon Angioplasty in the Atherosclerotic Rabbit*, Liu, et al., *Circulation*, vol. 81, No. 3, Mar. 1990.

*DNA Delivery from Polymer Matrices for Tissue Engineering* Shea, et al., *Nature Biotechnology*, vol. 17, Jun. 1999.

*Polymeric System for Dual Growth Factor Delivery*, Richardson, et al., *Nature Biotechnology*, vol. 19, Nov. 2001.

*Controlled Growth Factor Release from Synthetic Extracellular Matrices* Lee, et al., *Nature*, vol. 408, Dec. 21/28, 2000.

*Progress in Cardiovascular Disease*, Sonnenblick, et al., Sep./Oct. 1996.

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

Matsuda, 2002. Device-directed therapeutic drug delivery systems. Journal of Controlled Release, vol. 78:125-131.

Regar et al., 2001. Stent development and local drug delivery. British Medical Bulletin, vol. 59:277-248.

Needles, Sutures and Knots, Part III; Specific Suture Materials Al Sherbeeny,M., MD, vol. 1, Jul. 2004.

\* cited by examiner

BIODEGRADABLE DEVICE

The present invention is a continuation-in-part of U.S. patent application Ser. No. 10/209,591 filed Jul. 31, 2002 now abandoned, which in turn is a continuation-in-part of U.S. patent application Ser. No. 10/039,816 filed Oct. 26, 2001 now abandoned. The present invention is also a continuation-in-part of U.S. patent application Ser. No. 11/283,434 filed on Nov. 18, 2005 now U.S. Pat. No. 8,070,796 which claims priority on U.S. provisional Application Ser. Nos. 60/629,397 filed Nov. 19, 2004 and 60/658,411 filed Mar. 3, 2005. The present invention is also a continuation-in-part of U.S. patent application Ser. No. 11/283,330 filed on Nov. 18, 2005 now U.S. Pat. No. 7,967,855 which claims priority on U.S. provisional Application Ser. Nos. 60/629,470 filed Nov. 19, 2004 and 60/658,374 filed Mar. 3, 2005. The present invention is also a continuation-in-part of U.S. patent application Ser. No. 11/337,225 filed Jan. 20, 2006, which in turn is a continuation-in-part of U.S. patent application Ser. No. 10/209,591 filed Jul. 31, 2002 now abandoned, which in turn is a continuation-in-part of U.S. patent application Ser. No. 10/039,816 filed Oct. 26, 2001 now abandoned. The present invention is also a continuation-in-part of U.S. patent application Ser. No. 11/283,434 filed on Nov. 18, 2005 now U.S. Pat. No. 8,070,796 which claims priority on U.S. provisional Application Ser. Nos. 60/629,397 filed Nov. 19, 2004 and 60/658,411 filed Mar. 3, 2005.

The invention relates generally to devices, and particularly to an implant for use within a body, and more particularly to expandable graphs, stents, and/or other suitable devices which are useful in repairing various types of body passageways. These types of devices are useful in repairing blood vessels narrowed, occluded, dissected, or exhibiting vascular malformations (e.g., aneurysms and arterial venular malformations), and/or associated with disease or injury. The device at least partially includes a novel biodegradable polymer and the device is constructed at least partially using microfabrication and/or micromachining technology used in creating Micro-Electro-Mechanical Systems (MEMS), coating technologies, and/or molding processes with one or more agents.

BACKGROUND OF THE INVENTION

Medical treatment of various illnesses or diseases commonly includes the use of one or more devices. Two types of devices that commonly used to repair various types of body passageways are expandable grafts or stents (device). An expandable graft often contains one or more materials used in creating a mock lumen. These devices have been implanted in various areas of the mammalian anatomy. One purpose of a stent is to open a blocked or partially blocked body passageway. When a stent, graft, and/or other suitable device is used in a blood vessel, the stent, graft, and/or other suitable device is used to open the occluded vessel to achieve improved blood flow which is necessary to provide for the anatomical function of a tissue mass or organ. The procedure of opening a blocked or partially blocked body passageway commonly included the use of one or more stent, graft, and/or other suitable devices in combination with other accessory devices such as, but not limited to, an introducer sheath, a guiding catheter, a guide wire, an angioplasty balloon, etc. Similarly grafts have been used to open a blocked or partially blocked body passageway in addition to providing the added benefit of a mock lumen. The mock lumen has been useful in excluding dissections of the vasculature, encapsulating vulnerable plaque, and/or to exclude blood flow into vascular malformations.

Various physical attributes of a stent and/or graft contribute directly to the success rate of the device. These physical attributes included but are not limited to radiopacity, hoop strength, radial force, thickness of the device, dimensions associated with the device or accessory product required to deliver, biocompatibility of the materials, the influence of the device on the reoccurrence of the disease, and the ability to redirect blood flow. Cobalt and chromium and stainless steel alloys have been commonly used to form stents and/or grafts and Polytetrafluoroethylene (PTFE) has been commonly used as a graft material. These materials have been commonly used since such materials having a known history of safety and biocompatibility.

These materials however have limited physical performance characteristics as to size, strength, weight, bendability, biostability, radiopacity, and incorporation of the device. The materials commonly used to form prior stents and/or grafts are biostable materials that remain as a permanent implant in the blood vessel long after the stent and/or graft had achieved its function. As such, the continued presence of the device in the blood vessel is associated with an increased risk of thrombosis, in-stent restenosis, vascular narrowing, restenosis in the blood vessel at the location of the device, and/or reoccurrence of the vascular malformation. The presence of the device in the blood vessel also created a potential obstruction to later medical procedures attempting to correct problems in a body passageway upstream from the device. Devices were also prone to fracturing over time, especially when implanted in regions exposed to bending (e.g., leg, arms, neck, etc.). The repeated bending of the device has resulted in one or more portions fracturing creating emboli, and/or an increased rate of thrombosis. These fractures (e.g., strut fractures, fractures in graft material, etc.) could result in damage to the blood vessel and/or one or more regions of the vascular system downstream of the device.

The present invention is generally directed to a device that is at least partially formed of novel biodegradable or bioabsorbable polymer. The device of the present invention can also include one or more agents. The one or more agents can be used to enhance one or more physical properties of a device so as to improve the success rate of such device. The device can be at least partially formed by using microfabrication and/or micromachining technology used in creating Micro-Electro-Mechanical Systems (MEMS), coating technologies, and/or molding processes so as to overcome several of the past problems associated with such devices. The terms "biodegradable" or "bioabsorbable" are used interchangeably in this invention.

SUMMARY OF THE INVENTION

The previously mentioned shortcomings of prior devices are addressed by the novel device of the present invention. The device of the present invention is generally directed to a biodegradable polymer and/or a device partially formed using microfabrication and/or micromachining technology used in creating Micro-Electro-Mechanical Systems (MEMS), coating technologies, and/or molding processes in conjunction with one or more agents. The device in accordance with the present invention can be in the form of many different devices such as, but are not limited to stent, endovascular graft, surgical grafts (e.g., vascular grafts, etc.), orthopedic implants, staples, sheaths, guide wires, balloon catheters, hypotubes, catheters, polymer scaffolds for tissue regeneration, etc. In one non-limiting embodiment, the device is directed for use in a body passageway. As used herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, subarachnoid space, and central and peripheral nerve conduits, etc.). The techniques employed to deliver the device to a treatment area include, but are not limited to angioplasty, vascular anastomoses, transplantation, implantation, surgical implantation, subcutaneous introduction, minimally invasive surgical procedures, interventional procedures, and any combinations thereof. For vascular applications, the term "body passageway" primarily refers to blood vessels and chambers in the heart. The device can be an expandable stent and/or graft suitable for endovascular delivery and expandable by a balloon and/or other means (e.g., by its own internal forces "self expandable"). The stent, graft, and/or other suitable device can have many shapes and forms. Such shapes can include, but are not limited to stents, grafts, and/or other devices disclosed in U.S. Pat. Nos. or Publication Nos. 6,206,916; 6,436,133; 6,776,794; 6,805,707; 6,955,686; 2002/0032478; 2002/0045935; 2004/0093076; 2004/0093077; 2004/0172128; 2005/0004657; 2005/0075716; 2006/0009836; 2006/0085059; 2006/0100690; 2006/0106452; 2006/0106453; 2006/0142843; D481,139; and all the prior art cited in these patents and patent publications. These various designs and configurations of devices in such patents and patent publications are incorporated herein by reference.

When the device is in the form of a stent and/or graft the device is designed to be maneuvered into a treatment area (e.g., body passageway, etc.) and then expanded in the treatment area to enable better or proper fluid flow through the body passageway. The device can be formed of a material that at least partially dissolves in and/or is at least partially absorbed by the body over time so that the body passageway is eventually free of one or more portions of the device. As such, the device has at least partially fixed or repaired the obstruction or partially obstructed body passageway the device can be designed to at least partially dissolve in and/or be at least partially absorbed by the body so that the body passageway is at least partially free of the device. By at least partially eliminating the device from the body passageway, potential problems with thrombosis, in-stent restenosis, vascular narrowing, and/or restenosis in the body passageway in and/or around at the treatment location of the device is reduced or eliminated. Such elimination or partial elimination of the device from the body passageway also can result in the complete or partial elimination of a potential obstruction in the body passageway potentially compromising the ability to perform future procedures in the body passageway.

When the device is in the form of a stent and/or graft, the stent and/or graft is designed to be maneuvered into a treatment area (e.g., body passageway, etc.) and then expanded in the treatment area to enable better or proper fluid flow through the body passageway, provide structural support to a dissection in the vessel wall, provide structural support to venerable plaque within the vessel, and/or exclude vascular malformations. Additionally, the stent and/or graft can help to provide a lattice for the formation of an integral endothelial layer. Once the stent and/or graft has achieved its function, the stent and/or graft can be formed of a material that at least partially dissolves in and/or is at least partially absorbed by the body over time so that the body passageway is eventually free of one or more portions of the stent and/or graft. As such, after the stent and/or graft has at least partially fixed the disease or repaired the problem, the stent and/or graft can be designed to at least partially dissolve in and/or be at least partially absorbed by the body so that the body passageway is at least partially free of the stent and/or graft. By at least partially removing the stent and/or graft from the body passageway, potential problems with thrombosis, in-stent restenosis, vascular narrowing, reoccurrence of vascular malformation, and/or restenosis in the body passageway in and/or around at the treatment location of the stent and/or graft is reduced or eliminated. Such removal or partial removal of the stent and/or graft from the body passageway also can result in the complete or partial removal of a potential obstruction in the body passageway for potentially future procedures in the body passageway.

The biodegradability of one or more portions of the device can also fully or partially solve problems associated with fracturing of one or more portions of the device. For instance, when the device is the form of a stent and/or graft that is located in a region subjected to bending (e.g., leg, arms, neck, etc.), the repeated bending may cause one or more portions of the device fracture. Over time, one or more fatigued portions of the device may become dislodged from the device. These fractures (e.g., strut and/or graft fractures, etc.) and/or dislodged portions of the device can result in damage to the body passageway and/or one or more regions downstream of the device. The biodegradability of one or more portions of the device can facilitate in at least partially overcoming this problem since regions of the device prone to fractures and/or dislodgment (i.e., high strain regions) can be formed of a material that at least degrades or is absorbed over time, thus at least partially removing itself from the body passageway of the patient. The biodegradable material is formulated to at least partially dissolve in the body and/or be at least partially absorbed by the body after some period of time (e.g., one month, one year, ten years, etc.) and/or after one or more events (e.g., microfracture, fracture, break, exposure to one or more forms of electromagnetic radiation, exposure to a certain voltage and/or current, exposure to certain sound waves, exposure to certain chemicals and/or agents, etc.). As can be appreciated, the device could be at least partially formed of a material that can be caused to dissolve and/or be absorbed in the body and/or cause accelerated rates of dissolving and/or absorption in the body. In such a situation, the device could be caused to begin and/or be caused to accelerate in dissolving and/or bodily absorption so as to at least partially remove the stent, graft, and/or other suitable device, graft, and/or other suitable device from a body passageway to enable another device to be inserted in the body passageway. As can be appreciated, after the other device is inserted, a new device could be reinserted if so needed. As has been illustrated in these few non-limiting examples, there are numerous applications of device of the present invention. It will be appreciated that devices other than stents and/or grafts can have many advantages by being partially or fully formed by a biodegradable polymer. For example, experiments have shown limited success in the regeneration of nerve tissue where a nerve has been severed and then attached to either ends of a biodegradable and/or bioabsorbable polymer neurotube.

In one non-limiting aspect of the invention, the device can be in the form of, but is not limited to stents, grafts, vascular grafts, valves, orthopedic implants, sheaths, guide wires, balloon catheters, hypotubes, catheters, polymer scaffolds for neural regeneration, etc.

In another and/or alternative non-limiting aspect of the invention, the device can be designed such that once the device has at least partially achieved one or more of its functions, one or more portions of the device at least partially dissolves in and/or is at least partially absorbed by the body. The dissolving and/or bodily absorbing of one or more portions of the device can occur naturally and/or be activated and/or controlled by one or more degradation events. In one non-limiting example, the natural dissolving and/or bodily absorbing of one or more portions of the device can be achieved by the selection of one or more materials that naturally dissolving and/or are bodily absorbed when inserted in a particular portion of a body. As can be appreciated, one or more coatings can be used to control the time period that one or more portions of the device begin to dissolve and/or be absorbed and/or substantially completely dissolved and/or absorbed; however, this is not required. In another and/or alternative one non-limiting example, one or more portions of the device and/or device with coating can be caused to dissolve and/or be absorbed and/or accelerate in dissolving and/or being bodily absorbed during and/or after exposure to one or more events. Such degradation events include, but are not limited to, microfracture, fracture, and/or break in one or more portions of the device, exposure of the device to one or more forms of electromagnetic radiation, exposure of the device to one or more forms of particle radiation, exposure of the device to one or more forms of thermal energy, exposure of the device to a certain voltage and/or current, exposure of the device to certain sound waves; exposure of the device to one or more chemicals, and/or exposure of the device to one or more agents delivered in part either systemically and/or locally.

In another and/or alternative non-limiting aspect of the invention, one or more portions of the device are at least partially formed of one or more materials and coated with one or more materials that upon device microfracture, fracture, and/or break and begin to dissolve and/or be absorbed and/or accelerate in dissolving and/or being bodily absorption of the device. In another and/or alternative non-limiting example, one or more portions of the device are at least partially formed of one or more materials that begin and/or accelerate in dissolving and/or are bodily absorption when one or more portions of the device microfracture, fracture and/or break. In one non-limiting design, one or more portions of the device are coated with one or more materials that are biostable or slowly dissolve and/or are bodily absorbed. When one or more portions of the device microfracture, fracture and/or break, the one or more materials under the coating material is formulated to have a higher rate of dissolving and/or bodily absorption, thus the microfracture, fracture and/or break results in acceleration of one or more portions of the device to dissolve and/or bodily adsorb.

In a further and/or alternative non-limiting aspect of the present invention, the device can be in the form of a stent and/or graft. The device can have one or more body members, wherein each body member includes first and second ends and a wall surface disposed between the first and second ends. Each body member can have a first cross-sectional area which permits delivery of the body member into a body passageway, and a second, expanded cross-sectional area. The expansion of the device body member can be accomplished in a variety of manners. Typically, the body member is expanded to its second cross-sectional area by a radially, outwardly extending force applied at least partially from the interior region of the body member (e.g., by use of a balloon, etc.); however, this is not required. When the second cross-sectional area is variable, the second cross-sectional area is typically dependent upon the amount of radially outward force applied to the body member. The device can be designed such that the body member expands while retaining the original length of the body member; however, this is not required. The body member can have a first cross-sectional shape that is generally circular so as to form a substantially tubular body member; however, the body member can have other cross-sectional shapes. When the device includes two or more body members, the two or more body members can be connected together by at least one connector member. The device can include rounded, smooth and/or blunt surfaces to minimize and/or prevent damage to a body passageway as the device is inserted and/or maneuvered into a body passageway and/or expanded in a body passageway; however, this is not required. The device can be treated with gamma, beta and/or ebeam radiation, and/or otherwise sterilized; however, this is not required. The device can have multiple sections having a uniform and/or differing architectural configuration. Each of the sections of the device can be formed of a single part or formed of multiple parts which have been attached. When a section is formed of multiple parts, typically the section is formed into one continuous piece; however, this is not required.

In yet another and/or alternative non-limiting aspect of the present invention, the device is at least partially made of one or more polymers that are biodegradable (i.e., dissolves, degrades, is bodily absorbed, or any combination thereof in the body). The biodegradable polymer can form a portion of the device or the complete device. Generally, at least about 0.1 weight percent of the device and up to the complete device can be formed of one or more biodegradable polymers. It can also be appreciated that one or more materials coated on and/or impregnated in the device can be biodegradable or biostable. Such other materials can include, but are not limited to polymers, woven and non-woven fabrics, fibers, metal materials, marker materials, agents, adhesive, etc. The one or more biodegradable polymers that at least partially form the device can be a single polymer or be a combination of different polymers. The one or more biodegradable polymers selected to form one or more portions of the device are used to form a device having the desired physical characteristics of the device to achieve the designed purpose of the device (e.g., radial strength, flexibility, tinsel strength, longitudinal lengthening, deliverability, rate of absorption and/or degradation etc.). The one or more biodegradable polymers used to at least partially form the device are typically selected to withstand the manufacturing process that is needed to be accomplished in order to produce the device. These manufacturing processes can include, but are not limited to, laser cutting, etching, microfabrication and/or micromachining technology used in creating Micro-Electro-Mechanical Systems (hereafter referred to as MEMS technology), masking processes, crimping, annealing, drawing, pilgering, electro-plating, electro-polishing, chemical polishing, ion beam deposition or implantation, sputter coating, vacuum deposition, molding, melting, adhesive bonding, cutting, extruding, etching, heating, cooling, rotating mold deposition, etc. Rotating mold deposition is a process where a negative of the device design is created within the inner diameter of a hollow cylindrical mold and a polymeric solvent mixture is injected into the inner diameter of the mold. The cylindrical loaded mold is then rotated so as to drive the polymeric solvent mixture into the depths of the mold and cause the solvent portion of the mixture to evaporate. The aforementioned rotating mold deposition can occur in at least one step and the mold can be comprised of one or more sections containing at least one or more bioabsorbable polymer and/or one or more agent. The aforementioned rotating mold deposition will contain at least one device pattern but not limited to the use of multiple device patterns within a single mold.

In still a further and/or alternative non-limiting aspect of the present invention, one or more portions of the device can include, contain and/or be coated with one or more agents that are used to facilitate in the success of the device and/or treatment area. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to viral, fungus and/or bacteria infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; nerve repair; neural regeneration and/or the like. Non-limiting examples of agents that can be used include, but are not limited to, 5-Fluorouracil and/or derivatives thereof; 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular Ca2+ transport such as L-type (e.g., diltiazem, nifedipine, verapamil, etc.) or T-type Ca2+ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; anti-biotics; anti-coagulant compounds and/or derivatives thereof; anti-fibrosis compounds and/or derivatives thereof; antifungal compounds and/or derivatives thereof; anti-inflammatory compounds and/or derivatives thereof; Anti-Invasive Factor and/or derivatives thereof; anti-metabolite compounds and/or derivatives thereof (e.g., staurosporin, trichothecenes, and modified diphtheria and ricin toxins, *Pseudomonas* exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, Ca2+/calmodulin kinase II, casein kinase II, etc.); aspirin and/or derivatives thereof; azathioprine and/or derivatives thereof; $-Estradiol and/or derivatives thereof; $-1-anticollagenase and/or derivatives thereof; calcium channel blockers and/or derivatives thereof; calmodulin antagonists and/or derivatives thereof (e.g., H7, etc.); CAPTOPRIL and/or derivatives thereof; cartilage-derived inhibitor and/or derivatives thereof; ChIMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and/or derivatives thereof; endothelin and/or derivatives thereof endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein IIb/IIIa platelet membrane receptor antibody and/or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the IP3 receptor and/or derivatives thereof; inhibitors of the sodium/hydrogen antiporter and/or derivatives thereof (e.g., amiloride and derivatives thereof, etc.); insulin and/or derivatives thereof; Interferon alpha 2 Macroglobulin and/or derivatives thereof; ketoconazole and/or derivatives thereof; Lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; Plasminogen Activator Inhibitor-1 and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, H3P32O4, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; TH1 and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anti-coagulant peptide and/or derivatives thereof; thioprotese inhibitors and/or derivatives thereof; thyroid hormone and/or derivatives thereof; Tissue Inhibitor of Metalloproteinase-1 and/or derivatives thereof; Tissue Inhibitor of Metalloproteinase-2 and/or derivatives thereof; tissue plasma activators; TNF and/or derivatives thereof, tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the agent can include one or more derivatives of the above listed compounds and/or other compounds. In one non-limiting embodiment, the agent includes, but is not limited to, trapidil, Trapidil derivatives, taxol, taxol derivatives (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.), cytochalasin, cytochalasin derivatives (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.), paclitaxel, paclitaxel derivatives, rapamycin, rapamycin derivatives, 5-Phenylmethimazole, 5-Phenylmethimazole derivatives, GM-CSF (granulo-cytemacrophage colony-stimulating-factor), GM-CSF derivatives, statins or HMG-CoA reductase inhibitors forming a class of hypolipidemic agents, combinations, or analogs thereof, or combinations thereof. The type and/or amount of agent included in the device and/or coated on the device can vary. When two or more agents are included in and/or coated on the device, the amount of two or more agents can be the same or different. The type and/or amount of agent included on, in and/or in conjunction with the device are generally selected to address one or more clinical events. Typically the amount of agent included on, in and/or used in conjunction with the device is about 0.01-100 ug per mm$^2$ and/or at least about 0.01 weight percent of device; however, other amounts can be used. In one non-limiting embodiment of the invention, the device can be partially of fully coated and/or impregnated with one or more agents to facilitate in the success of a particular medical procedure. The amount of two of more agents on, in and/or used in conjunction with the device can be the same or different. The one or more agents can be coated on and/or impregnated in the device by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition. In another and/or alternative non-limiting embodiment of the invention, the type and/or amount of agent included on, in and/or in conjunction with the device is generally selected for the treatment of one or more clinical events. Typically the amount of agent included on, in and/or used in conjunction with the device is about 0.01-100 ug per mm$^2$ and/or at least about 0.01-100 weight percent of the device; however, other amounts can be used. The amount of two or more agents on, in and/or used in conjunction with the device can be the same or different. For instance, portions of the device to provide local and/or systemic delivery of one or more agents in and/or to a body passageway to a) inhibit or prevent thrombosis, in-stent restenosis, vascular narrowing and/or restenosis after the device has been inserted in and/or connected to a body passageway, b) at least partially passivate, remove, encapsulate, and/or dissolve lipids, fibroblast, fibrin, etc. in a body passageway so as to at least partially remove such materials and/or to passivate such vulnerable materials (e.g., vulnerable plaque, etc.) in the body passageway in the region of the device and/or downstream of the device. As can be appreciated, the one or more agents can have many other or additional uses. In still another and/or alternative non-limiting example, the device is coated with and/or includes one or more agents such as, but not limited to agents associated with thrombolytics, vasodilators, anti-hypertensive agents, antimicrobial or anti-biotic, anti-mitotic, anti-proliferative, anti-secretory agents, non-steroidal anti-inflammatory drugs, immunosuppressive agents, growth factors and growth factor antagonists, endothelial growth factors and growth factor antagonists, antitumor and/or chemotherapeutic agents, anti-polymerases, anti-viral agents, anti-body targeted therapy agents, hormones, anti-oxidants, biologic components, radio-therapeutic agents, radiopaque agents and/or radio-labeled agents. In addition to these agents, the device can be coated with and/or include one or more agents that are capable of inhibiting or preventing any adverse biological response by and/or to the device that could possibly lead to device failure and/or an adverse reaction by human or animal tissue. A wide range of agents thus can be used.

In a further and/or alternative non-limiting aspect of the present invention, the one or more agents on and/or in the device, when used on the device, can be released in a controlled manner so the area in question to be treated is provided with the desired dosage of agent over a sustained period of time. As can be appreciated, controlled release of one or more agents on the device is not always required and/or desirable. As such, one or more of the agents on and/or in the device can be uncontrollably released from the device during and/or after insertion of the device in the treatment area. It can also be appreciated that one or more agents on and/or in the device can be controllably released from the device and one or more agents on and/or in the device can be uncontrollably released from the device. It can also be appreciated that one or more agents on and/or in one region of the device can be controllably released from the device and one or more agents on and/or in the device can be uncontrollably released from another region on the device. As such, the device can be designed such that 1) all the agent on and/or in the device is controllably released, 2) some of the agent on and/or in the device is controllably released and some of the agent on the device is non-controllably released, or 3) none of the agent on and/or in the device is controllably released. The device can also be designed such that the rate of release of the one or more agents from the device is the same or different. The device can also be designed such that the rate of release of the one or more agents from one or more regions on the device is the same or different. Non-limiting arrangements that can be used to control the release of one or more agent from the device include a) at least partially coat one or more agents with one or more polymers, b) at least partially incorporate and/or at least partially encapsulate one or more agents into and/or with one or more polymers, c) insert one or more agents in pores, passageway, cavities, etc. in the device and at least partially coat or cover such pores, passageway, cavities, etc. with one or more polymers, and/or incorporate one or more agents in the one or more polymers that at least partially form the device. As can be appreciated, other or additional arrangements can be used to control the release of one or more agent from the device. The one or more polymers used to at least partially control the release of one or more agent from the device can be porous or non-porous. The one or more agents can be inserted into and/or applied to one or more surface structures and/or micro-structures on the device, and/or be used to at least partially form one or more surface structures and/or micro-structures on the device. As such, the one or more agents on the device can be 1) coated on one or more surface regions of the device, 2) inserted and/or impregnated in one or more surface structures and/or micro-structures, etc. of the device, and/or 3) form at least a portion or be included in at least a portion of the structure of the device. When the one or more agents are coated on the device, the one or more agents can, but is not required to, 1) be directly coated on one or more surfaces of the device, 2) be mixed with one or more coating polymers or other coating materials and then at least partially coated on one or more surfaces of the device, 3) be at least partially coated on the surface of another coating material that has been at least partially coated on the device, and/or 4) be at least partially encapsulated between a) a surface or region of the device and one or more other coating materials and/or b) two or more other coating materials. As can be appreciated, many other coating arrangements can be additionally or alternatively used. When the one or more agents are inserted and/or impregnated in one or more portions of the device, one or more surface structure and/or micro-structures of the device, and/or one or more surface structures and/or micro-structures of the device, 1) one or more other polymers can be applied at least partially over the one or more surface structure and/or micro-structures, surface structures and/or micro-structures of the device, 2) one or more polymers can be combined with one or more agents, and/or 3) one or more polymers can be coated over or more portions of the body of the device; however, this is not required. As such, the one or more agents can be 1) embedded in the structure of the device; 2) positioned in one or more surface structure and/or micro-structures of the device; 3) encapsulated between two polymer coatings; 4) encapsulated between the base structure and a polymer coating; 5) mixed in the base structure of the device that includes at least one polymer coating; or 6) one or more combinations of 1, 2, 3, 4 and/or 5. In addition or alternatively, the one or more coatings of the one or more polymers on the device can include 1) one or more coatings of non-porous polymers; 2) one or more coatings of a combination of one or more porous polymers and one or more non-porous polymers; 3) one or more coating of porous polymer, or 4) one or more combinations of options 1, 2, and 3. As can be appreciated different agents can be located in and/or between different polymer coating layers and/or on and/or the structure of the device. As can also be appreciated, many other and/or additional coating combinations and/or configurations can be used. In a further and/or alternative non-limiting embodiment of the present invention, the device can be embedded with and/or impregnated with one or more agents using a solvent to temporarily and/or permanently increase the porosity of the structure of a non-porous and/or porous polymer coating and/or device and be used to transport one or more agents into the matrix of the device. One or more solvents can be used to transport one or more agents. Solvent suitability is a function of compatibility with one or more agents and one or more materials of the device. Non-limiting examples of solvents include Dimethyl sulfoxide (DMSO), chloroform, ethylene, methanol, ethyl acetate, and the broader class of biocompatible or non-biocompatible solvents. The concentration of one or more agents, the type of polymer, the type and/or shape of surface structure and/or micro-structures in the device and/or the coating thickness of one or more agents can be used to control the release time, the release rate and/or the dosage amount of one or more agents; however, other or additional combinations can be used. As such, the agent and polymer system combination and location on the device can be numerous. As can also be appreciated, one or more agents can be deposited on the top surface of the device to provide an initial uncontrolled burst effect of the one or more agents prior to 1) the control release of the one or more agents through one or more layers of polymer system that include one or more nonporous polymers and/or 2) the uncontrolled release of the one or more agents through one or more layers of polymer system. The one or more agents and/or polymers can be coated on and/or impregnated in the device by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition. The thickness of each polymer layer and/or layer of agent is generally at least about 0.01 µm and is generally less than about 150 μm. In one non-limiting embodiment, the thickness of a polymer layer and/or layer of agent is about 0.02-75 μm, more particularly about 0.05-50 μm, and even more particularly about 1-30 μm. When the device includes and/or is coated with one or more agents such that at least one of the agents is at least partially controllably released from the device, the need or use of body-wide therapy for extended periods of time can be reduced or eliminated. In the past, the use of body-wide therapy was used by the patient long after the patient left the hospital or other type of medical facility. This body-wide therapy could last days, weeks, months or sometimes over a year after surgery. The device of the present invention can be applied or inserted into a treatment area and 1) merely requires reduced use and/or extended use of systemic therapy after application or insertion of the device or 2) does not require use and/or extended use of systemic therapy after application or insertion of the device. As can be appreciated, use and/or extended use of systemic therapy can be used after application or insertion of the device at the treatment area. In one non-limiting example, no body-wide therapy is needed after the insertion of the device into a patient. In another and/or alternative non-limiting example, short term use of systemic therapy is needed or used after the insertion of the device into a patient. Such short term use can be terminated after the release of the patient from the hospital or other type of medical facility, or one to two days or weeks after the release of the patient from the hospital or other type of medical facility; however, it will be appreciated that other time periods of systemic therapy can be used. As a result of the use of the device of the present invention, the use of systemic therapy after a medical procedure involving the insertion of a device into a treatment area can be significantly reduced or eliminated.

In another and/or alternative non-limiting aspect of the present invention, controlled release of one or more agents from the device, when controlled release is desired, can be accomplished by using one or more non-porous polymer layers and/or by use of one or more biodegradable polymers used to at least partially form the device; however, other and/or additional mechanisms can be used to controllably release the one or more agents. The one or more agents can be at least partially controllably released by molecular diffusion through the one or more non-porous polymer layers and/or from the one or more biodegradable polymers used to at least partially form the device. When one or more non-porous polymer layers are used, the one or more polymer layers are typically biocompatible polymers; however, this is not required. One or more non-porous polymers can be applied to the device without the use of chemical, solvents, and/or catalysts; however, this is not required. In one non-limiting example, the non-porous polymer can be at least partially applied by, but not limited to, vapor deposition and/or plasma deposition. The non-porous polymer can be selected so as to polymerize and cure merely upon condensation from the vapor phase; however, this is not required. The application of the one or more nonporous polymer layers can be accomplished without increasing the temperature above ambient temperature (e.g., 65-90° F.); however, this is not required. The non-porous polymer system can be mixed with one or more agents prior to being formed into at least a portion of the device and/or be coated on the device, and/or be coated on a device that previously included one or more agents; however, this is not required. The use or one or more non-porous polymers allows for accurate controlled release of the agent from the device. The controlled release of one or more agents through the nonporous polymer is at least partially controlled on a molecular level utilizing the motility of diffusion of the agent through the non-porous polymer. In one non-limiting example, the one or more non-porous polymer layers can include, but are not limited to, polyamide, parylene (e.g., parylene C, parylene N) and/or a parylene derivative.

In still another and/or alternative non-limiting aspect of the present invention, controlled release of one or more agents from the device, when controlled release is desired, can be accomplished by using one or more polymers that form a chemical bond with one or more agents. In one non-limiting example, at least one agent includes trapidil, trapidil derivative or a salt thereof that is covalently bonded to at least one polymer such as, but not limited to, an ethylene-acrylic acid copolymer. The ethylene is the hydrophobic group and acrylic acid is the hydrophilic group. The mole ratio of the ethylene to the acrylic acid in the copolymer can be used to control the hydrophobicity of the copolymer. The degree of hydrophobicity of one or more polymers can also be used to control the release rate of one or more agents from the one or more polymers. The amount of agent that can be loaded with one or more polymers may be a function of the concentration of anionic groups and/or cationic groups in the one or more polymers. For agents that are anionic, the concentration of agent that can be loaded on the one or more polymers is generally a function of the concentration of cationic groups (e.g. amine groups and the like) in the one or more polymer and the fraction of these cationic groups that can ionically bind to the anionic form of the one or more agents. For agents that are cationic (e.g., trapidil, etc.), the concentration of agent that can be loaded on the one or more polymers is generally a function of the concentration of anionic groups (i.e., carboxylate groups, phosphate groups, sulfate groups, and/or other organic anionic groups) in the one or more polymers, and the fraction of these anionic groups that can ionically bind to the cationic form of the one or more agents. As such, the concentration of one or more agents that can be bound to the one or more polymers can be varied by controlling the amount of hydrophobic and hydrophilic monomer in the one or more polymers, by controlling the efficiency of salt formation between the agent, and/or the anionic/cationic groups in the one or more polymers. In still another and/or alternative non-limiting aspect of the present invention, controlled release of one or more agents from the device, when controlled release is desired, can be accomplished by using one or more polymers that include one or more induced cross-links. These one or more cross-links can be used to at least partially control the rate of release of the one or more agents from the one or more polymers. The cross-linking in the one or more polymers can be instituted by a number of techniques such as, but not limited to, using catalysts, using radiation, using heat, and/or the like. The one or more cross-links formed in the one or more polymers can result in the one or more agents to become partially or fully entrapped within the cross-linking, and/or form a bond with the cross-linking. As such, the partially or fully agent takes longer to release itself from the crosslinking, thereby delaying the release rate of the one or more agents from the one or more polymers. Consequently, the amount of agent, and/or the rate at which the agent is released from the device over time can be at least partially controlled by the amount or degree of cross-linking in the one or more polymers. In still a further and/or alternative aspect of the present invention, a variety of polymers can be coated on the device and/or be used to form at least a portion of the device. The one or more polymers can be used on the medical for a variety of reasons such as, but not limited to, 1) forming a portion of the device, 2) improving a physical property of the device (e.g., improve strength, improve durability, improve biocompatibility, reduce friction, etc.), 3)

forming a protective coating on one or more surface structures on the device, 4) at least partially forming one or more surface structures on the medical device, and/or 5) at least partially controlling a release rate of one or more agents from the device. As can be appreciated, the one or more polymers can have other or additional uses on the device. The one or more polymers can be porous, non-porous, biostable, biodegradable (i.e., dissolves, degrades, is absorbed, or any combination thereof in the body), and/or biocompatible. When the device is coated with one or more polymers, the polymer can include 1) one or more coatings of non-porous polymers; 2) one or more coatings of a combination of one or more porous polymers and one or more non-porous polymers; 3) one or more coatings of one or more porous polymers and one or more coatings of one or more non-porous polymers; 4) one or more coatings of porous polymer, or 5) one or more combinations of options 1, 2, 3 and 4. The thickness of one or more of the polymer layers can be the same or different. When one or more layers of polymer are coated onto at least a portion of the device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers that can be coated on the device and/or used to at least partially form the device can be polymers that are considered to be biodegradable; polymers that are considered to be biostable; and/or polymers that can be made to be biodegradable and/or biodegradable with modification. Non-limiting examples of polymers that are considered to be biodegradable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L (lactic acid) and/or poly-D Lactic acid) and/or copolymers thereof (e.g. DL-PLA), with and without additives (e.g. calcium phosphate glass), and/or other copolymers (e.g., poly(caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-covalerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethylester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/or copolymers, blends, and/or composites of above. Non-limiting examples of polymers that considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-bstyrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g. polystyrene); poly(vinyl ethers) (e.g. polyvinyl methyl ether); poly(vinyl ketones); poly(vinylidene halides) (e.g. polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g. polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g. polyvinyl acetate); and/or copolymers, blends, and/or composites of above. Non-limiting examples of polymers that can be made to be biodegradable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used. The one or more polymers can be coated on and/or impregnated in the device by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold. The thickness of each polymer layer is generally at least about 0.01 µm and is generally less than about 150 µm; however, other thicknesses can be used. In one non-limiting embodiment, the thickness of a polymer layer and/or layer of agent is about 0.02-75 μm, more particularly about 0.05-50 μm, and even more particularly about 1-30 μm. As can be appreciated, other thicknesses can be used. In one non-limiting embodiment, the device has a body of which a majority is formed of a biodegradable polymer system and that at least a portion of the body includes and/or is coated with parylene, PLGA, POE, PGA, PLLA, PAA, PEG, chitosan and/or copolymers, blends, and/or composites of above and/or derivatives of one or more of these polymers. In another and/or alternative non-limiting embodiment, the device has a body of which a majority is formed of a biodegradable polymer system and that at least a portion of the body includes and/or is coated with a nonporous polymer that includes, but is not limited to, polyamide, parylene c, parylene n and/or a parylene derivative. In still another and/or alternative non-limiting embodiment, the device has a body of which a majority is formed of a biodegradable polymer system and that at least a portion of the body includes and/or is coated with poly(ethylene oxide), poly(ethylene glycol), and poly(propylene oxide), polymers of silicone, methane, tetrafluoroethylene (including TEFLON brand polymers), tetramethyldisiloxane, and the like.

In another and/or alternative non-limiting aspect of the present invention, the device, when including and/or is coated with one or more agents, can include and/or can be coated with one or more agents that are the same or different in different regions of the device and/or have differing amounts and/or concentrations in differing regions of the device. For instance, the device can a) be coated with and/or include one or more agents on at least one portion of the device and at least another portion of the device is not coated with and/or includes agent; b) be coated with and/or include one or more agents on at least one portion of the device that is different from one or more agents on at least another portion of the device; c) be coated with and/or include one or more agents at a concentration on at least one portion of the device that is different from the concentration of one or more agents on at least another portion of the device; etc.

In still another and/or alternative non-limiting aspect of the present invention, one or more surfaces of the device can be treated to achieve the desired coating properties of the one or more agents and one or more polymers coated on and/or incorporated in the device. Such surface treatment techniques include, but are not limited to, cleaning, buffing, smoothing, etching (chemical etching, plasma etching, etc.) achieved through a variety of techniques. When an etching process is used, various gasses can be used for such a surface treatment process such as, but not limited to, carbon dioxide, nitrogen, oxygen, Freon, helium, hydrogen, etc. The plasma etching process can be used to clean the surface of the device, change the surface properties of the device so as to affect the adhesion properties, lubricity properties, etc. of the surface of the device. As can be appreciated, other or additional surface treatment processes can be used prior to and/or after the coating of one or more agents and/or polymers on the surface of the device. In one non-limiting manufacturing process, one or more portions of the device are cleaned and/or plasma etched; however, this is not required. Plasma etching can be used to clean the surface of the device, and/or to form one or more non-smooth surfaces on the device to facilitate in the adhesion of one or more coatings of agents and/or one or more coatings of polymer on the device. Once one or more surface regions of the device have been treated, one or more coatings of polymer and/or agent can be applied to one or more regions of the device. For instance, 1) one or more layers of porous or non-porous polymer can be coated on an outer and/or inner surface of the device, 2) one or more layers of agent can be coated on an outer and/or interior surface of the device, or 3) one or more layers of porous or non-porous polymer that includes one or more agents can be coated on an outer and/or interior surface of the device. The one or more layers of agent can be applied to the device by a variety of coating techniques (e.g., dipping, rolling, brushing, spraying, particle atomization, etc.). One non-limiting coating technique is by an ultrasonic mist coating process wherein ultrasonic waves are used to break up the droplet of agent and form a mist of very fine droplets. These fine droplets have an average droplet diameter of about 0.1-3 microns. The fine droplet mist facilitates in the formation of a uniform coating thickness and can increase the coverage area on the device.

In still yet another and/or alternative non-limiting aspect of the present invention, one or more portions of the device can 1) include the same or different agents, 2) include the same or different amount of one or more agents, 3) include the same or different polymer coatings, 4) include the same or different coating thicknesses of one or more polymer coatings, 5) have one or more portions of the device controllably release and/or uncontrollably release one or more agents, and/or 6) have one or more portions of the device controllably release one or more agents and one or more portions of the device uncontrollably release one or more agents.

In yet another and/or alternative non-limiting aspect of the invention, the device can include a marker material that facilitates enabling the device to be properly positioned in a body passageway. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.). In one non-limiting embodiment, the marker material is visible to x-rays (i.e., radiopaque). The marker material can form all or a portion of the device and/or be coated on one or more portions (flaring portion and/or body portion; at ends of device; at or near transition of body portion and flaring section; etc.) of the device. The location of the marker material can be on one or multiple locations on the device. The size of the one or more regions that include the marker material can be the same or different. The marker material can be spaced at defined distances from one another so as to form ruler-like markings on the device to facilitate in the positioning of the device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. When the marker material is a flexible material, the marker material typically is formed of one or more polymers that are marker materials in-of-themselves and/or include one or more metal powders and/or metal compounds. In one non-limiting embodiment, the flexible marker material includes one or more metal powders in combinations with parylene, PLGA, POE, PGA, PLLA, PAA, PEG, chitosan and/or derivatives of one or more of these polymers.

In another and/or alternative non-limiting embodiment, the flexible marker material includes one or more metals and/or metal powders of aluminum, barium, bismuth, cobalt, copper, chromium, gold, iron, stainless steel, titanium, vanadium, nickel, zirconium, niobium, lead, molybdenum, platinum, yttrium, calcium, rare earth metals, magnesium, rhenium, zinc, silver, depleted radioactive elements, tantalum and/or tungsten; and/or compounds thereof. The marker material can be coated with a polymer protective material; however, this is not required. When the marker material is coated with a polymer protective material, the polymer coating can be used to 1) at least partially insulate the marker material from body fluids, 2) facilitate in retaining the marker material on the device, 3) at least partially shielding the marker material from damage during a medical procedure and/or 4) provide a desired surface profile on the device. As can be appreciated, the polymer coating can have other or additional uses. The polymer protective coating can be a biostable polymer or a biodegradable polymer (e.g., degrades and/or is absorbed). The coating thickness of the protective coating polymer material, when used, is typically less than about 300 microns; however, other thickness can be used. In one non-limiting embodiment, the protective coating materials include parylene, PLGA, POE, PGA, PLLA, PAA, PEG, chitosan and/or copolymers, blends, and/or composites of above and/or derivatives of one or more of these polymers.

In a further and/or alternative non-limiting aspect of the present invention, the device or one or more regions of the device can be constructed by use of one or more microfabrication and/or micromachining technology used in creating Micro-Electro-Mechanical Systems (MEMS, e.g., micromachining, laser micro machining, micro-molding, etc.); however, other or additional manufacturing techniques can be used. The device can include one or more surface structures (e.g., pore, channel, pit, rib, slot, notch, bump, teeth, well, hole, groove, etc.). These structures can be at least partially formed by MEMS technology and/or other types of technology. The device can include one or more micro-structures (e.g., micro-needle, micro-pore, micro-cylinder, micro-cone, micro-pyramid, micro-tube, microparallelopiped, micro-prism, micro-hemisphere, teeth, rib, ridge, ratchet, hinge, zipper, zip-tie like structure, etc.) on the inner, outer, or edge surface of the device. Non-limiting examples of structures that can be formed on the devices such as stent, graft, and/or other suitable devices are illustrated in United States Patent Publication Nos. 2004/0093076 and 2004/0093077, which are incorporated herein by reference. Typically, the micro-structures, when formed, extend from or into the outer surface no more than about 1000 microns, and more typically less than about 1000 microns; however, other sizes can be used. The micro-structures can be clustered together or disbursed throughout the surface of the device. Similar shaped and/or sized micro-structures and/or surface structures can be used, or different shaped and/or sized microstructures can be used. When one or more surface structures and/or micro-structures are designed to extend from the outer and/or inner surface of the device, the one or more surface structures and/or micro-structures can be formed in the extended position and/or be designed so as to extend from the device during and/or after deployment of the device in a treatment area. The micro-structures and/or surface structures can be designed to contain one or more agents and/or be connected to a passageway, cavity, etc. containing one or more agents; however, this is not required. The one or more surface structures and/or micro-structures can be used to engage and/or penetrate surrounding tissue or organs once the device has been positioned on and/or in a patient; however, this is not required. In another further and/or alternative non-limiting aspect of the present invention, the micro-structures and/or surface structures can be design to modify surface friction between the device and/or additional devices. For example, micro-structures and/or surface structures created on the inner surface of the device may be used to increase retention of a stent, graft, and/or other suitable device on a delivery catheter. In another further and/or alternative non-limiting aspect of the present invention, the micro-structures and/or surface structures can be design to create a system of undulations and/or crevasses used to facilitate growth of tissue. In one non-limiting aspect, the micro-structures and/or surface structures can be created on a film that could further be rolled into a shunt for neural regeneration, where the micro-structures and/or surface structures can provide a lattice to support and/or facilitate nerve growth. The one or more surface structures and/or micro-structures can be used to facilitate in forming or maintaining a shape of a device (i.e., see devices in United States Patent Publication Nos. 2004/0093076 and 2004/0093077). The one or more surface structures and/or micro-structures can be at least partially formed by MEMS technology, however, this is not required. In one non-limiting embodiment, the one or more surface structures and/or microstructures can be at least partially formed of an agent, polymer, agent polymer mixture, and/or layering of polymer and agent. One or more of the surface structures and/or micro-structures can include one or more internal passageways that can include one or more materials (e.g., agent, polymer, etc.); however, this is not required. In another further and/or alternative non-limiting aspect of the present invention, one or more internal passageways can be either connected and/or separated in part. The one or more surface structures and/or micro-structures can be formed by a variety of processes (e.g., machining, chemical modifications, chemical reactions, MEMS technology, etching, laser cutting, etc.). The one or more coatings and/or one or more surface structures and/or micro-structures of the device can be used for a variety of purposes such as, but not limited to, 1) increasing the bonding and/or adhesion of one or more agents, adhesives, marker materials and/or polymers to the device, 2) changing the appearance or surface characteristics of the device, and/or 3) controlling the release rate of one or more agents. The one or more microstructures and/or surface structures can be biostable, biodegradable, etc. One or more regions of the device that are at least partially formed by MEMS technology can be biostable, biodegradable, etc. The device or one or more regions of the device can be at least partially covered and/or filled with a protective material so as to at least partially protect one or more regions of the device, and/or one or more microstructures and/or surface structures on the device from damage. One or more regions of the device, and/or one or more micro-structures and/or surface structures on the device can be damaged when the device is 1) packaged and/or stored, 2) unpackaged, 3) connected to and/or otherwise secured and/or placed on another device, 4) inserted into a treatment area, 5) handled by a user, and/or 6) form a barrier between one or more micro-structures and/or surface structures and fluids in the body passageway. As can be appreciated, the device can be damaged in other or additional ways. The protective material can be used to protect the device and one or more micro-structures and/or surface structures from such damage. The protective material can include one or more polymers previously identified above. The protective material can be 1) biostable and/or biodegradable and/or 2) porous and/or non-porous. In one non-limiting design, the polymer is at least partially biodegradable so as to at least partially expose one or more micro-structure and/or surface structure to the environment after the device has been at least partially inserted into a treatment area. In another and/or additional non-limiting design, the protective material includes, but is not limited to, sugar (e.g., glucose, fructose, sucrose, etc.), carbohydrate compound, salt (e.g., NaCl, etc.), parylene, PLGA, POE, PGA, PLLA, PAA, PEG, chitosan and/or copolymers, blends, and/or composites of above and/or derivatives of one or more of these polymers; however, other and/or additional materials can be used. In still another and/or additional non-limiting design, the thickness of the protective material is generally less than about 300 microns, and typically less than about 150 microns; however, other thicknesses can be used depending upon the material chose of the protective material. The protective material can be coated by one or more mechanisms previously described herein.

In still yet another and/or alternative non-limiting aspect of the present invention, the device can include and/or be used with a physical hindrance. The physical hindrance can include, but is not limited to, an adhesive, a sheath, a magnet, tape, wire, string, etc. The physical hindrance can be used to 1) physically retain one or more regions of the device in a particular form or profile, 2) physically retain the device on a particular deployment device, 3) protect one or more surface structures and/or micro-structures on the device, and/or 4) form a barrier between one or more surface regions, surface structures and/or microstructures on the device and the fluids in a body passageway. As can be appreciated, the physical hindrance can have other and/or additional functions. The physical hindrance is typically a biodegradable material; however, a biostable material can be used. The physical hindrance can be designed to withstand sterilization of the device; however, this is not required. The physical hindrance can be applied to, included in and/or be used in conjunction with one or more devices. Additionally or alternatively, the physical hindrance can be designed to be used with and/or in conjunction with a device for a limited period of time and then 1) disengage from the device after the device has been partially or fully deployed and/or 2) dissolve and/or degrade during and/or after the device has been partially or fully deployed; however, this is not required. Additionally or alternatively, the physical hindrance can be designed and be formulated to be temporarily used with a device to facilitate in the deployment of the device; however, this is not required. In one non-limiting use of the physical hindrance, the physical hindrance is designed or formulated to at least partially secure a device to another device that is used to at least partially transport the device to a location for treatment. In another and/or alternative nonlimiting use of the physical hindrance, the physical hindrance is designed or formulated to at least partially maintain the device in a particular shape or form until the device is at least partially positioned in a treatment location. In still another and/or alternative nonlimiting use of the physical hindrance, the physical hindrance is designed or formulated to at least partially maintain and/or secure one type of device to another type of medical instrument or device until the device is at least partially positioned in a treatment location. The physical hindrance can also or alternatively be designed and formulated to be used with a device to facilitate in the use of the device. In one non-limiting use of the physical hindrance, when in the form of an adhesive, can be formulated to at least partially secure a device to a treatment area so as to facilitate in maintaining the device at the treatment area. For instance, the physical hindrance can be used in such use to facilitate in maintaining a device on or at a treatment area until the device is properly secured to the treatment area by sutures, stitches, screws, nails, rod, etc.; however, this is not required. Additionally or alternatively, the physical hindrance can be used to facilitate in maintaining a device on or at a treatment area until the device has partially or fully accomplished its objective. The physical hindrance is typically a biocompatible material so as to not cause unanticipated adverse effects when properly used. The physical hindrance can be biostable or biodegradable (e.g., degrades and/or is absorbed, etc.). When the physical hindrance includes or is one or more adhesives, the one or more adhesives can be applied to the device by, but is not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition on the device. The physical hindrance can also or alternatively form at least a part of the device. One or more regions and/or surfaces of a device can also or alternatively include the physical hindrance. The physical hindrance can include one or more agents and/or other materials (e.g., marker material, polymer, etc.); however, this is not required. When the physical hindrance is or includes an adhesive, the adhesive can be formulated to controllably release one or more agents in the adhesive and/or coated on and/or contained within the device; however, this is not required. The adhesive can also or alternatively control the release of one or more agents located on and/or contained in the device by forming a penetrable or non-penetrable barrier to such agents; however, this is not required. The adhesive can include and/or be mixed with one or more polymers; however, this is not required. The one or more polymers can be used to 1) control the time of adhesion provided by said adhesive, 2) control the rate of degradation of the adhesive, and/or 3) control the rate of release of one or more agents from the adhesive and/or diffusing or penetrating through the adhesive layer; however, this is not required. When the physical hindrance includes a sheath, the sheath can be designed to partially or fully encircle the device. The sheath can be designed to be physically removed from the device after the device is deployed to a treatment area; however, this is not required. The sheath can be formed of a biodegradable material that at least partially degrades over time to at least partially expose one or more surface regions, micro-structures and/or surface structures of the device; however, this is not required. The sheath can include and/or be at least partially coated with one or more biological agents. The sheath includes one or more polymers; however, this is not required. The one or more polymers can be used for a variety of reasons such as, but not limited to, 1) forming a portion of the sheath, 2) improving a physical property of the sheath (e.g., improve strength, improve durability, improve biocompatibility, reduce friction, etc.), and/or 3 at least partially controlling a release rate of one or more agents from the sheath. As can be appreciated, the one or more polymers can have other or additional uses on the sheath.

In still another and/or alternative non-limiting aspect of the invention, the device can be used in conjunction with one or more other agents that are not on the device. For instance, the success of the device can be improved by infusing, injecting or consuming orally one or more agents. Such agents can be the same and/or different from the one or more agents on and/or in the device. Such use of one or more agents are commonly used in systemic treatment of a patient after a medical procedure such as systemic therapy after the device has been inserted in the treatment area can be reduced or eliminated by use of the novel alloy. Although the device of the present invention can be designed to reduce or eliminate the need for long periods of systemic therapy after the device has been inserted in the treatment area, the use of one or more agents can be used in conjunction with the device to enhance the success of the device and/or reduce or prevent the occurrence of in-stent restenosis, vascular narrowing, and/or thrombosis and/or promote tissue growth (e.g., endothelium and/or neural tissue). For instance, solid dosage forms of agents for oral administration, and/or for other types of administration (e.g., suppositories, etc.) can be used. Such solid forms can include, but are not limited to, capsules, tablets, effervescent tablets, chewable tablets, pills, powders, sachets, granules and gels. The solid form of the capsules, tablets, effervescent tablets, chewable tablets, pills, etc. can have a variety of shapes such as, but not limited to, spherical, cubical, cylindrical, pyramidal, and the like. In such solid dosage form, one or more agents can be admixed with at least one filler material such as, but not limited to, sucrose, lactose or starch; however, this is not required. Such dosage forms can include additional substances such as, but not limited to, inert diluents (e.g., lubricating agents, etc.). When capsules, tablets, effervescent tablets or pills are used, the dosage form can also include buffering agents; however, this is not required. Soft gelatin capsules can be prepared to contain a mixture of the one or more agents in combination with vegetable oil or other types of oil; however, this is not required. Hard gelatin capsules can contain granules of the one or more agents in combination with a solid carrier such as, but not limited to, lactose, potato starch, corn starch, cellulose derivatives of gelatin, etc.; however, this is not required. Tablets and pills can be prepared with enteric coatings for additional time release characteristics; however, this is not required. Liquid dosage forms of the one or more agents for oral administration can include pharmaceutically acceptable emulsions, solutions, suspensions, syrups, elixirs, etc.; however, this is not required. In one non-limiting embodiment, when at least a portion of one or more agents is inserted into a treatment area (e.g., gel form, paste form, etc.) and/or provided orally (e.g., pill, capsule, etc.) and/or anally (suppository, etc.), one or more of the agents can be controllably released; however, this is not required. In one non-limiting example, one or more agents can be given to a patient in solid dosage form and one or more of such agents can be controllably released from such solid dosage forms. In another and/or alternative non-limiting example trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or analogs, or combinations thereof are given to a patient prior to, during and/or after the insertion of the device in a treatment area. Certain types of agents may be desirable to be present in a treated area for an extended period of time in order to utilize the full or nearly full clinical potential of the agent. For instance, Trapidil and/or trapidil derivatives is a compound that has many clinical attributes including, but not limited to, anti-platelet effects, inhibition of smooth muscle cells and monocytes, fibroblast proliferation and increased MAPK-1 which in turn deactivates kinase, a vasodilator, etc. These attributes can be effective in improving the success of a device that has been inserted at a treatment area. In some situations, these positive effects of trapidil and/or Trapidil derivatives need to be prolonged in a treatment area in order to achieve complete clinical competency. Trapidil and/or trapidil derivatives has a half life in vivo of about 2-4 hours with hepatic clearance of 48 hours. In order to utilize the full clinical potential of trapidil and/or trapidil derivatives, trapidil and/or trapidil derivatives should be metabolized over an extended period of time without interruption; however, this is not required. By inserting trapidil and/or trapidil derivatives in a solid dosage form, the trapidil and/or trapidil derivatives could be released in a patient over extended periods of time in a controlled manner to achieve complete or nearly complete clinical competency of the trapidil and/or trapidil derivatives. In another and/or alternative non-limiting example, one or more agents are at least partially encapsulated in one or more polymers. The one or more polymers can be biodegradable, non-biodegradable, porous, and/or non-porous. When the one or more polymers are biodegradable, the rate of degradation of the one or more biodegradable polymers can be used to at least partially control the rate at which one or more agents that are released into a body passageway and/or other parts of the body over time. The one or more agents can be at least partially encapsulated with different polymer coating thicknesses, different numbers of coating layers, and/or with different polymers to alter the rate at which one or more agents are released in a body passageway and/or other parts of the body over time. The rate of degradation of the polymer is principally a function of 1) the water permeability and solubility of the polymer, 2) chemical composition of the polymer and/or agent, 3) mechanism of hydrolysis of the polymer, 4) the agent encapsulated in the polymer, 5) the size, shape and surface volume of the polymer, 6) porosity of the polymer, 7) the molecular weight of the polymer, 8) the degree of cross-linking in the polymer, 9) the degree of chemical bonding between the polymer and agent, and/or 10) the structure of the polymer and/or agent. As can be appreciated, other factors may also affect the rate of degradation of the polymer. When the one or more polymers are biostable, the rate at when the one or more agents are released from the biostable polymer is a function of 1) the porosity of the polymer, 2) the molecular diffusion rate of the agent through the polymer, 3) the degree of cross-linking in the polymer, 4) the degree of chemical bonding between the polymer and agent, 5) chemical composition of the polymer and/or agent, 6) the agent encapsulated in the polymer, 7) the size, shape and surface volume of the polymer, and/or 8) the structure of the polymer and/or agent. As can be appreciated, other factors may also affect the rate of release of the one or more agents from the biostable polymer. Many different polymers can be used such as, but not limited to, aliphatic polyester compounds (e.g., PLA (i.e. poly(D, L-lactic acid), poly (L-lactic acid)), PLGA (i.e. poly(lactide-co-glycoside), etc.), POE, PEG, PLLA, parylene, chitosan and/or copolymers, blends, and/or composites of above and/or derivatives of one or more of these polymers. As can be appreciated, the at least partially encapsulated agent can be introduced into a patient by means other than by oral introduction, such as, but not limited to, injection, topical applications, intravenously, eye drops, nasal spray, surgical insertion, suppositories, intrarticularly, intraocularly, intranasally, intradermally, sublingually, intravesically, intrathecally, intraperitoneally, intracranially, intramuscularly, subcutaneously, directly at a particular site, and the like.

In another and/or non-limiting aspect of the invention, secondary substances can be combined in part with the polymer and/or agent as a mixture, substrate layer, or at least in part at particular places within the device to modify the degradation and/or absorption of the polymer and/or the release of at least one agent. In a non-limiting aspect of the invention the secondary substance can contain at least one hydrophobic and/or hydrophilic substance which include, but are not limited to, fats, oils, methacrylate or its derivatives, amphiphilc or its derivatives, and at least one biodegradable polymers.

In still another and/or alternative aspect of the invention, the device can be an expandable device that can be expanded by use of some other device (e.g., balloon, etc.) and/or is self expanding. The expandable device can be fabricated at least in part from a material that has no or substantially no shape memory characteristics or can be fabricated from a material having shape-memory characteristics. Typically, when one or more shape-memory materials are used, the shape memory material composition is selected such that the shape memory material remains in an unexpanded configuration at a cold temperature (e.g., below body temperature) and/or in a restrained configuration; however, this is not required. When the shape memory material is heated (e.g., to body temperature), the expandable body section can be designed to expand to at least partially seal and secure the device in a body passageway or other region; however, this is not required. In an alternate non-limiting aspect of the invention, the shape memory material is in a superelastic state and is not required to be heated in order to expand.

In yet another and/or alternative non-limiting aspect of the invention, the device is in the form of a stent, graft, and/or other suitable device. The stent, graft, and/or other suitable device can be an expandable stent, graft, and/or other suitable device that is expandable by a balloon and/or is self-expanding. The material used to form the stent, graft, and/or other suitable device is selected to withstand the manufacturing process that is needed to be accomplished in order to produce the stent, graft, and/or other suitable device. These manufacturing processes can include, but are not limited to, electroplating, MEMS technology, electro-polishing, chemical polishing, ion beam deposition or implantation, sputter coating, vacuum deposition, masking, molding, cutting, etching, and/or other coating processes. The device can have one or more body members. The one or more body members can include first and second ends and a wall surface disposed between the first and second ends. Typically, each body member has a first cross-sectional area which permits delivery of the body member into a body passageway, and a second, expanded cross-sectional area. The expansion of one or more body member of the device can be accomplished in a variety of manners. In one manner, one or more body members are expanded to the second cross-sectional area by a radially, outwardly extending force applied at least partially from the interior region of the body member (e.g., by use of a balloon, etc.). The body member can include heat sensitive and/or superelastic materials (e.g., shape memory materials, etc.) that expand upon exposure to heat, thus not requiring a radially, outwardly extending force applied at least partially from the interior region of the body member; however, such force can be used with such a body member. The second cross-sectional area of the device can be fixed or variable. The device can be designed such that one or more body members expand while substantially retaining the original longitudinal length of the body member; however, this is not required. The one or more body members can have a first cross-sectional shape that is generally circular so as to form a substantially tubular body member; however, the one or more body members can have other cross-sectional shapes. When the device includes two or more body members, the two or more body members can be connected together by at least one connector member. The device can include rounded, smooth and/or blunt surfaces to minimize and/or prevent damage to a body passageway as the device is inserted into a body passageway and/or expanded in a body passageway; however, this is not required. The device can be treated with gamma, beta and/or e-beam radiation, and/or otherwise sterilized; however, this is not required.

In still yet another and/or additional non-limiting aspect of the present invention, one or more portions of the device can include or be made of the agent and/or polymer. When the device is coated with one or more polymers, the polymer can include 1) one or more coatings of non-porous polymers; 2) one or more coatings of a combination of one or more porous polymers and one or more non-porous polymers; 3) one or more coatings of one or more porous polymers and one or more coatings of one or more nonporous polymers; 4) one or more coating of porous polymer, or 5) one or more combinations of options 1, 2, 3 and 4. The thickness of one or more of the polymer layers can be the same or different. Varying types and/or thickness of polymer layers can also be used.

In one non-limiting application of the present invention, there is provided a device designed to improve patient procedural outcome. The device can have one non-limiting advantage of delivering one or more agents into a treatment area (e.g., body passageway, etc.). For instance, the device can be designed to be inserted in and/or be connected to a body passageway (e.g., blood vessel, etc.) and which device inhibits or prevents thrombosis and/or one or more other diseases. The device can be designed to be used as agent delivery mechanism to deliver one or more agents to and/or into a wall of a body passageway and/or downstream from the site if implantation of the device. In one non-limiting design, the device is a stent, graft, and/or other suitable device comprised of a base material wherein one or more portions of the base material includes one or more biodegradable polymers. The stent, graft, and/or other suitable device also is coated with and/or includes one or more agents. One or more polymers can be used to partially control the release of the agent from the device; however, this is not required. In one non-limiting controlled release arrangement, molecular diffusion through a polymer is used to control the release rate of one or more agents from the device. When a molecular diffusion mechanism is used, one or more non-porous polymer layers can be used to facilitate in such molecular diffusion; however, this is not required. The molecular composition, molecular structure and/or coating thickness of the non-porous polymer can be selected to control the release rate of one or more agents from the device.

In another non-limiting application of the present invention, there is provided a medical device that is adapted for introduction into a patient. The device can have a variety of applications such as, but not limited to, placement into the vascular system, esophagus, trachea, colon, biliary tract, nervous system, or urinary tract or used as a replacement for native, synthetic, implanted or engineered organs, vessels, and/or neural tissue. As can be appreciated, the device can have other or additional uses. The device includes one or more biodegradable polymers. The biodegradable material can be dissolved, absorbed, degraded, or any combination thereof in the body. Various materials that can be used to form one or more portions of the device such as, but are not limited to, one or more metals and/or metal alloys (e.g., brass, calcium, carbon, chromium, cobalt, cobalt-chromium alloy, copper, gold, lead, magnesium, molybdenum, molybdenum-rhenium alloy, nickel, Nitinol, platinum, rare earth metals, rhenium, silver, stainless steel, tantalum, tantalum-tungsten alloy, titanium, tungsten, yttrium, zinc zirconium, etc.), fiber materials (e.g., carbon fiber composites, fiberglass, etc.) in combination with and/or polymers (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, polylactic acid, polyglycolic acid or copolymers thereof, a polyanhydride, polycaprolactone, polyhydroxy-butyrate valerate or another biodegradable polymer or mixtures or copolymers of these, a protein, an extracellular matrix component, collagen, POE (e.g., Translute™), PEVA, PBMA, PLGA, fibrin, polyethylene tetraphthalate (Dacron), expandable polytetrafluoroethylene (e.g., Gortex, Impra, etc.), polyurethane, etc.) and/or copolymers, blends, and/or composites of above and/or derivatives of one or more of these polymers. As can be appreciated, the device can be completely formed of polymer. One or more agents on and/or in the device can be released controllably and/or uncontrollably from the device. As such, all of the agents can be controllably released from the device, all of the agents can be uncontrollably released from the device, or one or more agents can be controllably released and one or more agents can be uncontrollably released from the device. The controlled release of the one or more agents from the device can be at least partially controlled by molecular diffusion through one or more non-porous polymer layers; however, it will be appreciated that other, or additional mechanism can be used to control the rate of release of one or more agents from the device. For instance, the one or more agents can be selected so as to be chemically bonded to one or more polymers and/or secondary substances to control the rate of release of one or more agents from the device; however, this is not required. The one or more polymers can include cross-links to control the rate of release of one or more agents from the device; however, this is not required. The one or more polymers and/or one or more agents can be hydrophobic or hydrophilic, thus can be used to facilitate in the controlled release of the one or more agents from the device; however, this is not required. The thickness of the one or more polymer layers can be selected to facilitate in the controlled release of the one or more agents; however, this is not required. The molecular weight and/or molecular structure of the one or more agents and/or one or more polymers can be selected to facilitate in the release of the one or more agents; however, this is not required. The device can be one or more polymers and/or one or more agents. The one or more polymers and/or agents can 1) form at least a portion of the device, 2) be coated on one or more regions of the device, and/or 3) be contained in one or more regions within the device. Non-limiting examples of polymers that can be used include parylene, PLGA, POE, PGA, PLLA, PAA, PEG, chitosan and/or copolymers, blends, and/or composites of above and/or derivatives of one or more of these polymers; however, other or additional polymers can be used. Many different agents can be used on the device. Such agents can include, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, analogs, or combinations thereof; however, it will be appreciated that other or additional agents can be used. The structure of the device during manufacture can be pre-treated to facilitate in the coating of one or more polymers and/or agents on the device; however, this is not required. The surface topography of the base structure of the device can be uniform or varied to achieve the desired operation and/or agent released from the device. As can be appreciated, one or more regions of the device can be constructed by use of one or more MEMS technology; however, this is not required. Materials that can be used by MEMS technology include, but are not limited to, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, and/or a PEG derivative and/or copolymers, blends, and/or composites of above and/or derivatives of one or more of these polymers. The device can include one or more surface structures, and/or micro-structures that includes one or more agents and/or polymers; however, this is not required. These structures can be at least partially formed by MEMS technology and/or other types of technology. The structures can be designed to contain and/or be fluidly connected to a passageway in the device that includes one or more agents; however, this is not required. The structures can be used to engage and/or penetrate surrounding tissue or organs once the device has be position on and/or in a patient; however, this is not required. The structures can be used to at least partially maintain the structure and/or form of the device; however, this is not required. One or more polymers and/or agents can be inserted in these structures and/or at least partially form these structures of the device. The structures can be clustered together or disbursed throughout the surface of the device. Similar shaped and/or sized structures can be used, or different shaped and/or sized structures can be used. Typically, the micro-structures, when formed, extend from or into the outer and/or inner surface no more than about 1000 microns, and more typically, less than about 1000 microns; however, other sizes can be used. The time period one or more agents are released from the device, when one or more agents are used, is typically dependent on the designed medical treatment and/or other factors. In one non-limiting arrangement, one or more agents are released from the device for at least several days after the device is inserted in the body of a patient; however, this is not required. In another one non-limiting arrangement, one or more agents are released from the device for at least about one week after the device is inserted in the body of a patient. In still another one non-limiting arrangement, one or more agents are released from the device for at least about two weeks after the device is inserted in the body of a patient. In yet another one non-limiting arrangement, one or more agents are released from the device for about one week to one year after the device is inserted in the body of a patient. As can be appreciated, the time frame that one or more of the agents can be released from the device can be longer or shorter. The time period for the release of two or more agents from the device can be the same or different. The type of the one or more agents used on the device, the release rate of the one or more agents from the device, and/or the concentration of the one or more agents being released from the device can be the same or different. The use of the device can be used in conjunction with other agents. For instance, the success of the device can be enhanced by infusing, injecting or consuming orally the same and/or different agent used for anti-platelet and/or anti-coagulation therapy that is being released controllably from the device. The introduction of agents from a source other than the device can have an enhanced or synergistic effect which can improve the success of the device. Solid dosage forms of agents for oral administration can be used. Such solid forms can include, but are not limited to, capsules, tablets, effervescent tablets, chewable tablets, pills, powders, sachets, granules and gels. In such solid dosage forms, the agent can be admixed with at least one filler material such as, but not limited to, sucrose, lactose or starch. Such dosage forms can also comprise, as in normal practice, additional substances such as, but not limited to, inert diluents (e.g., lubricating agents, etc.). When capsules, tablets, effervescent tablets or pills are used, the dosage form can also include buffering agents. Soft gelatin capsules can be prepared to contain a mixture of the agent in combination with at least one hydrophobic and/or hydrophilic substance not limited to fats, oils, methacrylate or its derivatives, amphiphilc or its derivatives, at least one biodegradable and/or bioabsorbable polymers. Hard gelatin capsules can contain granules of the agent in combination with a solid carrier such as, but not limited to, lactose, potato starch, corn starch, cellulose derivatives of gelatin, etc. Tablets and pills can be prepared with enteric coatings for additional time release characteristics. Liquid dosage forms of the agent for oral administration can include pharmaceutically acceptable emulsions, solutions, suspensions, syrups, elixirs, etc. Typically the introduction of one or more agents used for anti-platelet and/or anti-coagulation therapy from a source other than the device is limited to no more than about one day after the device has been implanted in a patient, and more typically no more than about one week after the device has been implanted in a patient, and even more typically, no more than about one month after the device has been implanted in a patient; however, it can be appreciated that periods of up to 2-3 months or more can be used.

One non-limiting object of the present invention is the provision of a device that is at least partially formed of a biodegradable polymer.

Another and/or alternative non-limiting object of the present invention is the provision of a device that is at least partially formed by MEMS technology.

Still another and/or alternative non-limiting object of the present invention is the provision of a device that is coated and/or impregnated with one or more agents.

Yet another and/or alternative object of the present invention is the provision of a device that at least partially controls the release rate of one or more agents.

Still yet another and/or alternative non-limiting object of the present invention is the provision of a device that includes one or more micro-structures on the outer surface of the device.

A further and/or alternative non-limiting object of the present invention is the provision of a device that improves procedural success rates.

Still a further and/or alternative non-limiting object of the present invention is the provision of a device that inhibits or prevents the occurrence of in-stent, graft, and/or other suitable device restenosis, vascular narrowing and/or restenosis after the device has been inserted into a body passageway.

Yet a further and/or alternative non-limiting object of the present invention is the provision of a device that passivates and/or excapsulates vulnerable plaque in a body passageway.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE DRAWINGS

Figure 1:
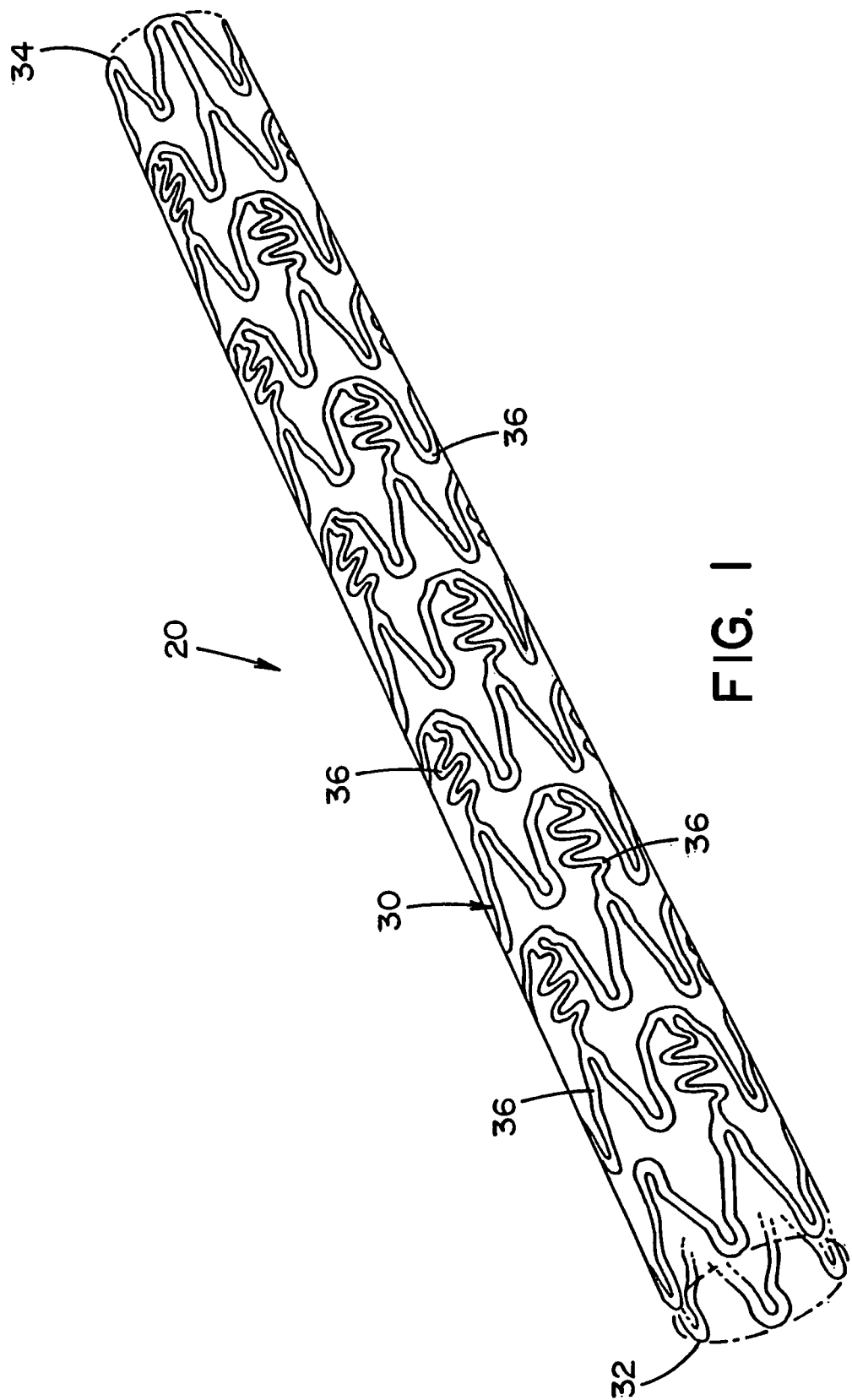
FIG. 1 is a perspective view of a section of a device in the form of an unexpanded stent, graft, and/or other suitable device which permits delivery of the stent, graft, and/or other suitable device into a body passageway.

Referring now to the drawings wherein the showings are for the purpose of illustrating embodiments of the invention only and not for the purpose of limiting the same, FIGS. 1-24 disclose a device in the form of a stent, graft, and/or other suitable device for use in a body passageway. The stent, graft, and/or other suitable device of the present invention can be at least partially formed of a biodegradable polymer. The stent, graft, and/or other suitable device of the present invention can at least partially dissolve in the body and/or be absorbed by the body. For instance, the stent, graft, and/or other suitable device can be designed to be inserted and/or placed in a diseased area in a body passageway and be expanded and/or attached in the diseased and/or damaged area. Once the stent, graft, and/or other suitable device has at least partially achieved its function, the stent, graft, and/or other suitable device can begin or become completely dissolved in and/or is absorbed by the body naturally and/or in response to one or more events so that the body passageway is at least partially free of the stent, graft, and/or other suitable device. The at least partial biodegradability of the stent, graft, and/or other suitable device can also fully or partially solve problems associated with micro-fracturing, fracturing and/or breaking off of one or more portions of the stent, graft, and/or other suitable device. For instance, when the stent, graft, and/or other suitable device is located in a region that is subject to bending, the repeated bending can eventually fatigue the materials that form the stent, graft, and/or other suitable device. Over time, one or more portions of the stent, graft, and/or other suitable device can micro-fracture, fracture and/or separate from the stent, graft, and/or other suitable device. These micro-fractures, fractures (e.g., strut fractures, etc.) and/or separated portions of the stent, graft, and/or other suitable device can result in irritation and/or damage to the body passageway and/or one or more regions of the body passageway (e.g., vascular system, etc.) downstream of the stent, graft, and/or other suitable device. The at least partial biodegradability of the stent, graft, and/or other suitable device can overcome this problem since such micro-fractures, fractures and/or separated portions of the stent, graft, and/or other suitable device at least partially degrade and/or are bodily absorbed over time and thus become at least partially removed from the body passageway of the patient. In one specific example, when the device is in the form of a stent, graft can include one or more agents that can be used to a) inhibit or prevent thrombosis, in-stent, graft, and/or other suitable device restenosis, vascular narrowing and/or restenosis, and/or b) passivate, remove, encapsulate and/or dissolve plaque, lipids, fibroblasts and/or fibrin in the region of the stent, graft, and/or other suitable device and/or downstream of the stent, graft, and/or other suitable device after the stent, graft, and/or other suitable device has been inserted into the blood vessel.

Figure 2:
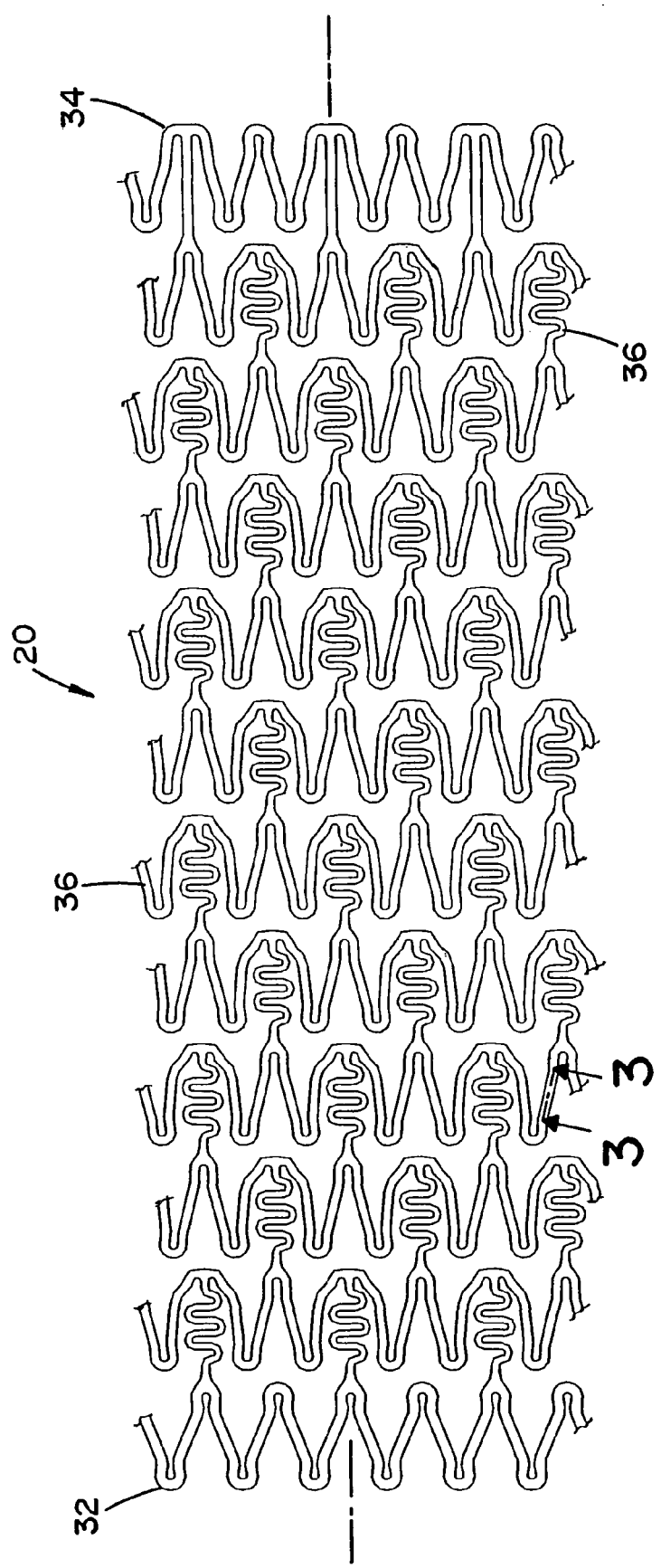
FIG. 2 is a sectional view of the stent, graft, and/or other suitable device of FIG. 1.

The device in the form of a stent, graft, and/or other suitable device as illustrated in FIGS. 1 and 2 is designed to be insertable in a diseased area in a body passageway and to expand the diseased area to enable better or proper fluid flow through the body passageway; however, the stent, graft, and/or other suitable device can be used for other or additional reasons. In one specific non-limiting example, the stent, graft, and/or other suitable device can be used to open an obstructed blood vessel. The stent, graft, and/or other suitable device can include and/or be used with one or more agents; however, this is not required. When one or more agents are used, the one or more agents can be used to inhibit thrombosis, in-stent, graft, and/or other suitable device restenosis, vascular narrowing and/or restenosis after the stent, graft, and/or other suitable device has been inserted into the blood vessel; however, this is not required. The one or more agents, when used, can also or alternatively be used to remove and/or dissolve lipids, fibroblast, fibrin, etc. from the blood vessel so as to at least partially clean the blood vessel of such substances in the region of the stent, graft, and/or other suitable device and/or downstream of the stent, graft, and/or other suitable device.

Although FIG. 1 illustrates the device in the form of a stent, graft, and/or other suitable device for use in the cardiovascular and/or surgical field, the device can be in other forms (e.g., vascular graft, sutures, staples, orthopedic implants, nail, rod, screw, neurological shunts and anatomists devices, etc.) and/or be used in other medical fields (e.g., orthopedic field, cardiology field, pulmonology field, urology field, nephrology field, gastroenterology field, gynecology field, otolaryngology field, neurology, etc.). The device, when used in the cardiovascular field, can be used to address various medical problems such as, but not limited to, restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications, wounds, myocardial infarction, pulmonary thromboembolism, cerebral thromboembolism, thrombophlebitis, thrombocytopenia and/or bleeding disorders. When the device is in the form of a stent, graft, and/or other suitable device, the stent, graft, and/or other suitable device can be expandable such as by a balloon and/or self expanding. The material that is used to form one or more portions of the device is typically selected to withstand the manufacturing process used to form the device (e.g., electroplating, electro polishing, extrusion, molding, EDM machining, MEMS technology, etching, molding, cutting, chemical polishing, ion beam deposition or implantation, sputter coating, vacuum deposition, plasma deposition, etc.). The device can include one or more surface structures and/or micro-structures; however, this is not required. Such structures can be formed by a variety of processes (e.g., machining, chemical modifications, chemical reactions, micro-machining, micro-molding, etching, etc.). The one or more coatings and/or one or more surface structures and/or micro-structures of the device, when used, can be used for a variety of purposes such as, but not limited to, 1) increasing the bonding and/or adhesion of one or more agents, adhesives, marker materials and/or polymers to the medical device, 2) changing the appearance or surface characteristics of the device, and/or 3) controlling the release rate of one or more agents. As can be appreciated, other or additional purposes can be achieved. The techniques employed to deliver the device include, but are not limited to, angioplasty, vascular anastomoses, transplantation, implantation, subcutaneous introduction, minimally invasive surgical procedures, injection, topical applications, bolus administration, infusion, interventional procedures, and any combinations thereof. When the device is in the form of a stent, graft, and/or other suitable device, the device can be inserted by techniques such as, but not limited to, balloon delivery, sheath catheter delivery, etc.

Referring again to FIGS. 1-2, there is disclosed a device in the form of a stent, graft, and/or other suitable device for a body passageway. The stent, graft, and/or other suitable device is an expandable stent, graft, and/or other suitable device for at least partially expanding occluded segments of a body passageway; however, the stent, graft, and/or other suitable device can have other or additional uses. For example, the expandable stent, graft, and/or other suitable device may be used for, but not limited to, such purposes as 1) a supportive stent, graft, and/or other suitable device for placement within a blocked vasculature opened by transluminal recanalization, which are likely to collapse in the absence of an internal support; 2) forming a catheter passage through the mediastinal and/or other veins occluded by inoperable cancers; 3) reinforcement of catheter created intrahepatic communications between portal and/or hepatic veins in patients suffering from portal hypertension; 4) a supportive stent, graft, and/or other suitable device for placement in the narrowing of the esophagus, the intestine, the ureter and/or the urethra; and/or 5) a supportive stent, graft, and/or other suitable device for reinforcement of reopened and/or previously obstructed bile ducts. Accordingly, use of the term "stent, graft, and/or other suitable device" encompasses the foregoing or other usages within various types of body passageways.

As illustrated in FIG. 1, the device 20 in the form of an expandable stent, graft, and/or other suitable device includes at least one tubular shaped body member 30 having a first end 32, a second end 34, and member structures 36 disposed between the first and second ends. FIG. 2 illustrates the stent, graft, and/or other suitable device prior to being formed into a generally tubular shape. As can be appreciated, the stent, graft, and/or other suitable device can be formed of a plurality of body members connected together. Body member 30 has a first diameter which permits delivery of the body member into a body passageway. The first diameter of the body member is illustrated as being substantially constant along the longitudinal length of the body member. As can be appreciated, the body member can have a varying first diameter along at least a portion of the longitudinal length of the body member. The body member also has a second expanded diameter, not shown. The second diameter typically varies in size; however, the second diameter can be non-variable in size. The stent, graft, and/or other suitable device can be expanded in a variety of ways such as by a balloon. A balloon expandable stent, graft, and/or other suitable device is typically pre-mounted or crimped onto an angioplasty balloon catheter. The balloon catheter is then positioned into the patient via a guide wire. Once the stent, graft, and/or other suitable device is properly positioned, the balloon catheter is inflated to the appropriate pressure for stent, graft, and/or other suitable device expansion. After the stent, graft, and/or other suitable device has been expanded, the balloon catheter is deflated and withdrawn, leaving the stent, graft, and/or other suitable device deployed at the treatment area.

Referring again to FIGS. 1-2, the stent, graft, and/or other suitable device can be formed of a variety of materials. The stent, graft, and/or other suitable device is generally is formed of biocompatible materials; however this is not required. The stent, graft, and/or other suitable device is at least partially formed of a polymer material that is biodegradable (i.e., dissolves, degrades, is absorbed, or any combination thereof in the body). A portion or all of the stent, graft, and/or other suitable device can be formed of a biodegradable polymer material. For instance, the body member 30 of stent, graft, and/or other suitable device 20 in FIGS. 1-2 can be fully or partially formed of the biodegradable polymer material. The material or materials used to form the stent, graft, and/or other suitable device include properties (e.g., strength, durability, hardness, biostability, bendability, coefficient of friction, radial strength, flexibility, tensile strength, longitudinal lengthening, stress-strain properties, improved recoil properties, radiopacity, heat sensitivity, biocapatability, etc.) that are selected to form a stent, graft, and/or other suitable device which promotes the success of the stent, graft, and/or other suitable device. The stent, graft, and/or other suitable device can be made of one piece or multiple pieces. The material that is used to form one or more portions of the stent, graft, and/or other suitable device is typically selected to withstand the manufacturing process used to form the stent, graft, and/or other suitable device.

Figure 3:
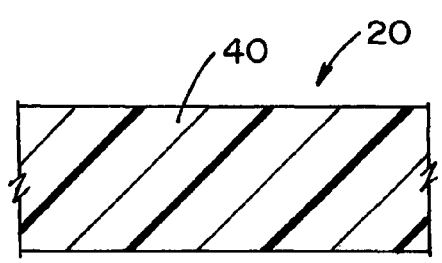
FIG. 3 is a cross-sectional view along line 3-3 of FIG. 2 illustrating a biodegradable material that forms the device.

Referring now to FIG. 3, a cross-section of a portion of stent, graft, and/or other suitable device 20 is illustrated which is formed of a biodegradable polymer material 40. The biodegradable polymer can include one or more polymers. Non-limiting examples of biodegradable polymers that can be used include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L (lactic acid) and/or poly-D Lactic acid) and/or copolymers thereof (e.g., DL-PLA), with and without additives (e.g., calcium phosphate glass), and/or other copolymers (e.g., poly (caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly (valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly (propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl-ester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly (amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/or copolymers, blends, and/or composites of above. The selection of the type and/or amount of biodegradable polymer material used to form the stent, graft, and/or other suitable device will generally depend on the particular application of the stent, graft, and/or other suitable device and the desired function of the stent, graft, and/or other suitable device. As can be appreciated, many types of biodegradable polymers can be used to at least partially form the stent, graft, and/or other suitable device. One or more materials (e.g., plasticizer, stabilizing agent, etc.) can be mixed with the one or more polymers to improve the physical properties of the stent, graft, and/or other suitable device. In one non-limiting example, a plasticizer (e.g., triacetin, etc.) can be added to alter the mechanical properties of the stent, graft, and/or other suitable device. As illustrated in FIG. 3, the biodegradable polymer material that is used to form at least a portion of stent, graft, and/or other suitable device 20 does not include any coatings. The surface of the biodegradable polymer material can be treated so as to have generally smooth surfaces. When the surface of the biodegradable polymer material is treated, typically one or more ends of the surfaces are treated by filing, buffing, polishing, grinding, coating, and/or the like to remove or reduce the number of rough and/or sharp surfaces; however, this is not required. The smooth surfaces of the stent, graft, and/or other suitable device can be used to reduce potential damage to surrounding tissue as the stent, graft, and/or other suitable device is positioned in and/or expanded in a body passageway.

Referring now to FIGS. 4-24, the stent, graft, and/or other suitable device can include one or more coatings and/or one or more surface structures and/or micro-structures. The one or more surface structures and/or micro-structures can be formed by a variety of processes (e.g., machining, chemical modifications, chemical reactions, MEMS technology, etching, laser cutting, etc.). The one or more coatings and/or one or more surface structures and/or micro-structures of the stent, graft, and/or other suitable device can be used for a variety of purposes such as, but not limited to, 1) increasing the bonding and/or adhesion of one or more agents, adhesives, marker materials and/or polymers to the stent, graft, and/or other suitable device, 2) changing the appearance or surface characteristics of the stent, graft, and/or other suitable device, and/or 3) controlling the release rate of one or more agents.

Figure 4:
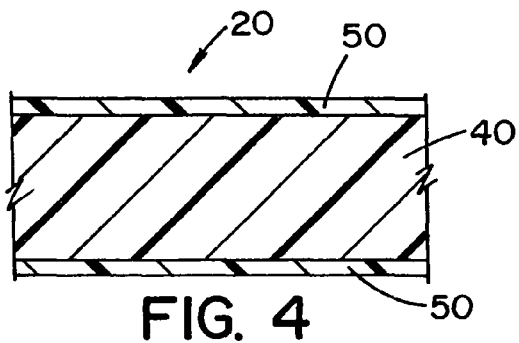
FIG. 4 is a cross-sectional view along line 3-3 of FIG. 2 illustrating the biodegradable material that forms the device that includes a polymer coating.

Referring to FIG. 4, the biodegradable polymer material 40 can be coated with a layer 50 of one or more agents or polymers that can be used to improve the functionality or success of the stent, graft, and/or other suitable device. The one or more agents or polymers. When the stent, graft, and/or other suitable device includes one or more polymer coatings as illustrated in FIG. 4, this polymer coating can be formed of a biodegradable or non-biodegradable material. The one or more polymer coatings can be porous or non-porous polymers. Non-limiting examples of the one or more polymers that can be coated on one or more regions of the biodegradable material 40 include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof. The one or more polymers can be used for a variety of purposes such as, but not limited to, 1) forming a desired surface profile on the surface of the stent, graft, and/or other suitable device, 2) affecting the rate of biodegradability of the stent, graft, and/or other suitable device when inserted in the body passageway, 3) protect the surface of the stent, graft, and/or other suitable device, 4) affecting the coefficient of friction of the surface of the stent, graft, and/or other suitable device, and/or 5) increasing the strength of the stent, graft, and/or other suitable device. As can be appreciated, the one or more polymers can have other or additional functions. The one or more agents can include, but are not limited to, antibiotic agents, anti-body targeted therapy agents, anti-hypertensive agents, anti-microbial agents, anti-mitotic agents, anti-oxidants, anti-polymerases agents, anti-proliferative agents, anti-secretory agents, anti-tumor agents, antiviral agents, bioactive agents, chemotherapeutic agents, cellular components, cytoskeletal inhibitors, drug, growth factors, growth factor antagonists, hormones, immunosuppressive agents, living cells, non-steroidal anti-inflammatory drugs, radioactive materials, radiotherapeutic agents, thrombolytic agents, vasodilator agents, etc. Non-limiting examples of agents that can be used include a vascular active agent that inhibits and/or prevents restenosis, vascular narrowing and/or in-stent, graft, and/or other suitable device restenosis such as, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, other or additional agents can be included on the stent, graft, and/or other suitable device to improve the functionality or success of the stent, graft, and/or other suitable device. The amount of agent delivered to a certain region of a patient's body can be controlled by varying the type of agent, the coating thickness of the agent, the drug concentration of the agent, the solubility of the agent, the location of the agent that is coated and/or impregnated on and/or in the stent, graft, and/or other suitable device, the amount of surface area of the stent, graft, and/or other suitable device that is coated and/or impregnated with the agent, the location of the agent on the stent, graft, and/or other suitable device, etc. When the medical device is in the form of a stent, graft, and/or other suitable device for use in the vascular system, the agent that is typically included, but not required, on and/or in the stent, graft, and/or other suitable device includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however, it will be appreciated that other or additional agents can be used. In addition, many other or additional agents can be included on and/or in the stent, graft, and/or other suitable device such as, but not limited to, the following categories of agents: thrombolytics, vasodilators, anti-hypertensive agents, antimicrobial or anti-biotic, anti-mitotic, anti-proliferative, anti-secretory agents, non-steroidal anti-inflammatory drugs, immunosuppressive agents, growth factors and growth factor antagonists, chemotherapeutic agents, anti-polymerases, anti-viral agents, anti-body targeted therapy agents, hormones, anti-oxidants, radio-therapeutic agents, radiopaque agents and/or radio-labeled agents.

The surface of the biodegradable material 40 can be treated to enhance the coating of the stent, graft, and/or other suitable device and/or to enhance the mechanical characteristics of the stent, graft, and/or other suitable device; however, this is not required. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon, helium, hydrogen, etc. The plasma etching process can be used to clean the surface of the stent, graft, and/or other suitable device, change the surface properties of the stent, graft, and/or other suitable device so as to affect the adhesion properties, lubricity properties, etc. of the surface of the stent, graft, and/or other suitable device. As can be appreciated, other or additional surface treatment processes can be used prior to the coating of one or more agents and/or polymers on the surface of the stent, graft, and/or other suitable device.

Referring now to FIGS. 5-8, there is illustrated several non-limiting combinations of agent and polymer that have been coated on the surface of the stent, graft, and/or other suitable device. As can be appreciated, other combinations of agent and polymer can be used. When one or more agents are coated on the stent, graft, and/or other suitable device, the one or more agents can be controllably released, uncontrollably released and/or immediately released from the stent, graft, and/or other suitable device to optimize their effects and/or to compliment the function and success of the stent, graft, and/or other suitable device. The controlled release can be accomplished by 1) controlling the size of the surface structures and/or micro-structures on the stent, graft, and/or other suitable device, and/or 2) using one or more polymer coatings; however, other or additional mechanisms can be used to control the release rate of one or more agents from the stent, graft, and/or other suitable device. For example, the amount of agent delivered to a certain region of a patient's body can be controlled by, but not limited to, one or more of the following: a) selecting the type of agent to be used on the stent, graft, and/or other suitable device, b) selecting the amount of agent to be used on the stent, graft, and/or other suitable device, c) selecting the coating thickness of the agent to be used on the stent, graft, and/or other suitable device, d) selecting the drug concentration of the agent to be used on the stent, graft, and/or other suitable device, e) selecting the solubility of the agent to be used on the stent, graft, and/or other suitable device, f) selecting the location the biological agent that is to be coated on the stent, graft, and/or other suitable device, g) selecting the amount of surface area of the stent, graft, and/or other suitable device that is coated with the agent, h) selecting the location of the agent on the stent, graft, and/or other suitable device, i) selecting the size, shape, amount and/or location of the one or more surface structures and/or micro-structures of the stent, graft, and/or other suitable device that include and/or are integrated with the agent, j) selecting the type and/or amount of polymer to be mixed with the agent, k) selecting the type, amount and/or coating thickness of the polymer coating used to at least partially coat and/or encapsulate the agent, etc. As can be appreciated, the amount of one or more agent delivered to a region of the body can be at least partially controlled in other or additional ways. The one or more agents can be combined with and/or at least partially coated with a polymer that affects the rate at which the agent is released from the stent, graft, and/or other suitable device; however, this is not required. The polymer coating can also or alternatively be used to assist in binding the one or more agents to the stent, graft, and/or other suitable device; however, this is not required. The polymer coating, when used, can be biodegradable or biostable. The polymer coating can be formulated to form a bond with the agent to the stent, graft, and/or other suitable device; however, this is not required. The one or more polymers used in the polymer coating and the one or more agents can be mixed together prior to being applied to the stent, graft, and/or other suitable device; however, this is not required. The one or more agents that are used in combination with a one or more polymers in the polymer coating can control the release of the agent by molecular diffusion; however, this is not required. The thickness of the polymer coating can be about 0.1-25; however, other coating thickness can be used. The time period the one or more agents are released from the stent, graft, and/or other suitable device can vary. The one or more agents, when used, can be coated on the surface of the stent, graft, and/or other suitable device, on the surface of one or more polymer layers, and/or mixed with one or more polymer layers. One or more agents can also be coated on the top surface of stent, graft, and/or other suitable device 20. At least one agent can be entrapped within and/or coated over with a non-porous polymer layer to at least partially control the release rate of the biological rate; however, this is not required. When a non-porous polymer layer is used on the stent, graft, and/or other suitable device, the non-porous polymer typically includes parylene C, parylene N, parylene F and/or a parylene derivative; however, other or additional polymers can be used. Various coating combinations can be used on the stent, graft, and/or other suitable device. For instance, a polymer layer that includes one or more polymers can be coated on the top of the layer of one or more agents; however, this is not required. In another example, the stent, graft, and/or other suitable device 20 can include a layer of one or more polymers. A layer of one or more biological agent can be coated on the top of the layer of one or more polymers; however, this is not required. Furthermore, one or more polymers can be coated on the layer of one or more agents; however, this is not required. As can be appreciated other coating combinations can be used. Generally, one or more agents are released from the stent, graft, and/or other suitable device for at least several days after the stent, graft, and/or other suitable device is inserted in the body of a patient; however, this is not required. Generally, one or more agents are released from the stent, graft, and/or other suitable device for at least about 1-7 days after the stent, graft, and/or other suitable device is inserted in the body of a patient, typically at least about 1-14 days after the stent, graft, and/or other suitable device is inserted in the body of a patient, and more typically about 1-365 days after the stent, graft, and/or other suitable device is inserted in the body of a patient; however, this is not required. As can be appreciated, the time frame that one or more of the agents are released from the stent, graft, and/or other suitable device can be shorter or longer. The time period for the release of two or more agents from the stent, graft, and/or other suitable device can be the same or different. The type of the one or more agents used on the stent, graft, and/or other suitable device, the release rate of the one or more agents from the stent, graft, and/or other suitable device, and/or the concentration of the one or more agents being released from the stent, graft, and/or other suitable device during a certain time period is typically selected to deliver the one or more agents to the area of treatment and/or disease. When the stent, graft, and/or other suitable device is used in the vascular system, the one or more agents can be used to inhibit or prevent thrombosis, restenosis, vascular narrowing and/or in-stent, graft, and/or other suitable device restenosis after the stent, graft, and/or other suitable device has been implanted; however, this is not required. When the stent, graft, and/or other suitable device is used in the vascular system, the agent that is generally included on and/or in the stent, graft, and/or other suitable device is, but not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however, it will be appreciated that other or additional agents can be used. In addition, many other or additional agents can be included on and/or in the stent, graft, and/or other suitable device such as, but not limited to, the following categories of agents: thrombolytics, vasodilators, anti-hypertensive agents, anti-microbial or anti-biotic, anti-mitotic, anti-proliferative, antisecretory agents, non-steroidal anti-inflammatory drugs, immunosuppressive agents, growth factors and growth factor antagonists, chemotherapeutic agents, anti-polymerases, anti-viral agents, anti-body targeted therapy agents, hormones, anti-oxidants, radio-therapeutic agents, radiopaque agents and/or radio-labeled agents.

Figure 5:
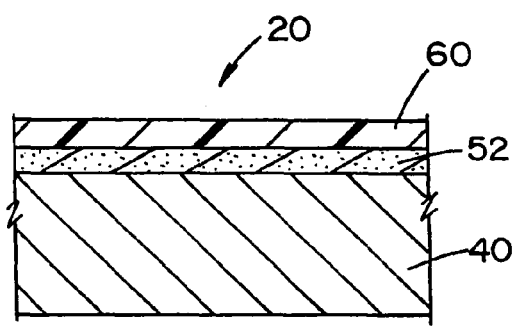
FIG. 5 is a cross-sectional view along line 3-3 of FIG. 2 illustrating one type of coating on a device.

Referring now to FIG. 5, the base structure 40 of the stent, graft, and/or other suitable device 20 includes a layer 52 of agent. The layer of agent can include one or more agents. In one non-limiting example, the agent includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GMCSF derivatives, or combinations thereof. A polymer layer 60 is coated on the top of layer 52. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more agents of layer 52 from stent, graft, and/or other suitable device 20. The one or more non-porous polymers can include, but is not limited to, parylene C, parylene N, parylene F and/or a parylene derivative.

Figure 6:
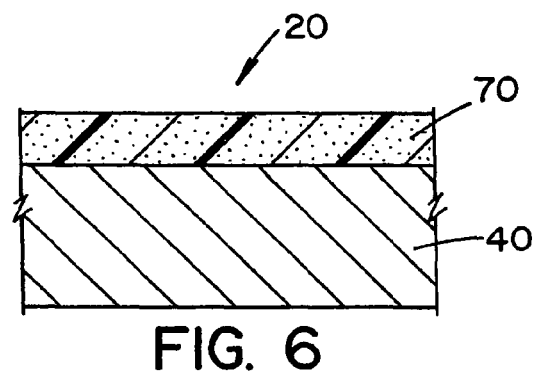
FIG. 6 is a cross-sectional view along line 3-3 of FIG. 2 illustrating another type of coating on a device.

As illustrated in FIG. 6, the base structure 40 of stent, graft, and/or other suitable device 20 includes a layer 70 of polymer and agent. Layer 70 can include one or more agents mixed with one or more polymers. In one non-limiting example, the one or more agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers can include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers included in layer 70 include a non-porous polymer to at least partially control a rate of release by molecular diffusion of the one or more agents in layer 70. The nonporous polymer can include, but is not limited to, parylene C, parylene N, parylene F and/or a parylene derivative.

Figure 7:
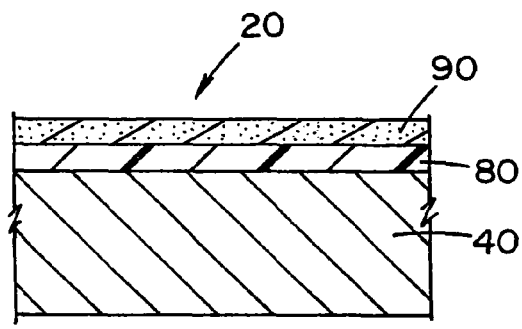
FIG. 7 is a cross-sectional view along line 3-3 of FIG. 2 illustrating another type of coating on a device.

As illustrated in FIG. 7, the base structure 40 of stent, graft, and/or other suitable device 20 includes a layer 80 of polymer. Layer 80 can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. The one or more non-porous polymers, when used, can include, but are not limited to, parylene C, parylene N, parylene F and/or a parylene derivative. A layer 90 of one or more agents is coated on top of polymer layer 80. Polymer layer 8 can be used to facilitate in the securing of layer 90 to the stent, graft, and/or other suitable device; however, this is not required. In one non-limiting example, the one or more agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of agent on the top surface of the stent, graft, and/or other suitable device can provide a burst of agent in the treatment area (e.g., body passageway, etc.) after insertion of the stent, graft, and/or other suitable device. In one non-limiting example, the one or more agents include trapidil and/or derivatives thereof.

Figure 8:
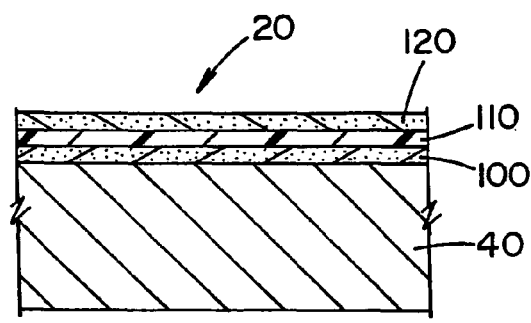
FIG. 8 is a cross-sectional view along line 3-3 of FIG. 2 illustrating another type of coating on a device.

As illustrated in FIG. 8, the base structure 40 of stent, graft, and/or other suitable device 20 includes a layer 100 of one or more agents. In one non-limiting example, the one or more agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. A polymer layer 110 is coated on the top of layer 100. The polymer layer can include one or more polymers. The polymer layer can include one or more porous polymers and/or non-porous polymers, and/or one or more biostable and/or biodegradable polymers. Nonlimiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more agents of layer 100 from stent, graft, and/or other suitable device 20. The one or more non-porous polymers can include, but are not limited to, parylene C, parylene N, parylene F and/or a parylene derivative. A layer 120 of agent is coated on top of polymer layer 110. Layer 120 can include one or more agents. In one non-limiting example, the one or more agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of biological agent on the top surface of the stent, graft, and/or other suitable device provide can provide a burst of one or more agents in the treatment area (e.g., body passageway, etc.) after insertion of the stent, graft, and/or other suitable device. In one nonlimiting example, the one or more agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, other combinations of polymer layer and layer of agent can be used on the stent, graft, and/or other suitable device. These other combinations are also encompassed within the scope of the present invention.

Figure 9:
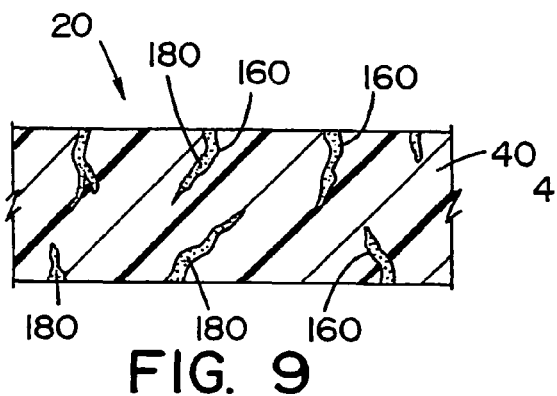
FIGS. 9 and 10 are a cross-sectional view along line 3-3 of FIG. 2 illustrating a biodegradable material that forms a device that includes a plurality of two types of pores and/or micro-pores in the biodegradable material which are filled with one or more agents.
Figure 10:
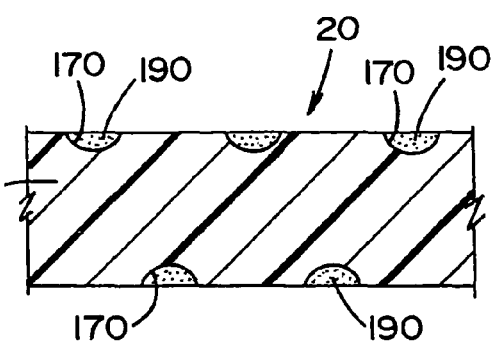

Referring now to FIG. 9, the base structure 40 of stent, graft, and/or other suitable device 20 includes a plurality of surface structures and/or micro-structures 160. The surface structures and/or micro-structures are illustrated as being formed in the base structure of the stent, graft, and/or other suitable device. As defined herein, a microstructure (e.g., micro-channel, micro-needle, micro-pore, etc.) is a structure that has at least one dimension (e.g., average width, average diameter, average height, average length, average depth, etc.) that is no more than about 2 mm, and typically no more than about 1 mm. The surface structures and/or micro-structures can be formed in the biodegradable material during the formation of the stent, graft, and/or other suitable device and/or from the surface treatment of the stent, graft, and/or other suitable device (e.g. etching, mechanical drill, etc.). In one non-limiting example, the stent, graft, and/or other suitable device is formed by MEMS technology and the surface structures and/or micro-structures are formed by MEMS technology. The surface structures and/or micro-structures are illustrated as being on the form of pores in the biodegradable material. As can be appreciated, many other structures can be formed in the biodegradable material. For instance, as illustrated in FIG. 10, the surface structures and/or micro-structures are in the form of pits or depressions 170. As illustrated in FIGS. 9 and 10, the surface structures and/or micro-structures 160, 170 include one or more agents 180, 190; however, it can be appreciated that one or more surface structures and/or microstructures can include a) a combination of polymer and agent, b) only a polymer, c) one agent, or d) nothing. In one non-limiting example, the one or more biological agents include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The size of the one or more surface structures and/or micro-structures can be used to at least partially control the rate of release of the agent and/or polymer from the one or more surface structures and/or micro-structures; however, this is not required. As can be appreciated, a layer that includes one or more agents or a combination of one or more agents and one or more polymers, not shown, can be coated in the surface of the biodegradable material; however, this is not required. This coating, if used, can include one or more the same or one or more different agents from the one or more agents in the surface structures and/or micro-structures. As can also be appreciated, additional coatings of agent and/or polymer, not shown, can be used. The polymer, when used, can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer includes one or more non-porous polymers to at least partially control a rate of release by molecular diffusion of the one or more agents from stent, graft, and/or other suitable device 20. The one or more non-porous polymers can include, but are not limited to, parylene C, parylene N, parylene F and/or a parylene derivative.

Figure 17:
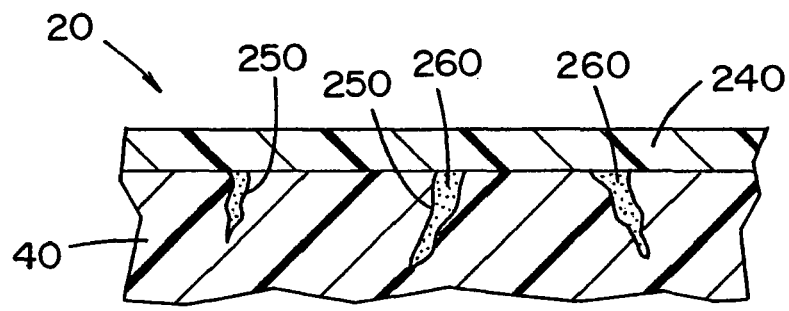
FIG. 17 is a cross-sectional view along line 3-3 of FIG. 2 illustrating a biodegradable material that forms a device that includes a plurality of two types of pores and/or micro-pores in the biodegradable material which are filled with one or more agents and covered with one or more polymer coatings.

As illustrated in FIG. 17, a polymer layer 240 is coated on the top surface of the biodegradable material 40. The polymer layer 240 covers the one or more agents 240 located in the surface structures and/or micro-structures 250. The polymer layer can include one or more polymers. The polymer layer can include a porous polymer and/or non-porous polymer. the polymer layer can include one or more agent; however, this is not required. The polymer layer can include a biostable and/or biodegradable polymer. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer includes one or more non-porous polymers to at least partially control a rate of release by molecular diffusion of the one or more agents from stent, graft, and/or other suitable device 20. The one or more non-porous polymers can include, but are not limited to, parylene C, parylene N, parylene F and/or a parylene derivative. The agent can include, but is not limited to, trapidil, Trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof.

Figure 11:
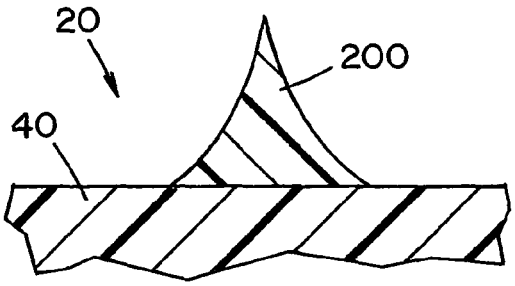
FIGS. 11 and 12 are a cross-sectional view along line 3-3 of FIG. 2 illustrating a biodegradable material that forms a device that includes one or more micro-needles on the surface of the stent, graft, and/or other suitable device.
Figure 12:
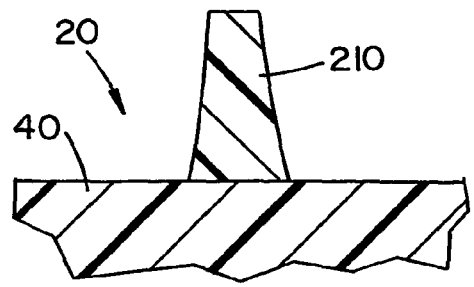
Figure 13:
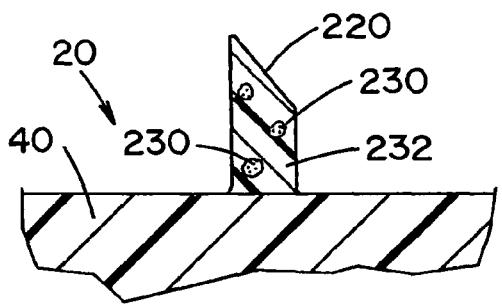
FIG. 13 is a cross-sectional view along line 3-3 of FIG. 2 illustrating a biodegradable material that forms a device that includes a plurality of micro-needles on the surface of the stent, graft, and/or other suitable device which are formed of one or more polymers and agents.

Referring now to FIGS. 11-13, the biodegradable material 40 of stent, graft, and/or other suitable device 20 includes one or more needles or micro-needles 100, 110, 120 formed on the surface of the stent, graft, and/or other suitable device. These needles or micro-needles can be formed by MEMS technology and/or by other processes. As illustrated in FIGS. 11-13, the needles or micro-needles can have a variety of shapes and sizes. The needles or micro-needles can be at least partially formed from one or more polymers and/or agents. It can be appreciated that the needles or micro-needles can be at least partially formed of other of additional material such as, but not limited to one or more adhesives, etc. As illustrated in FIG. 13, the needles or micro-needles include a combination of one or more polymers 132 and/or one or more agents 130. As can be appreciated, one or more layer of one or more agents and/or polymers can be coated on the needles or micro-needles; however, this is not required. When the one or more needles or micro-needles include and/or are coated with one or more agents, such agents can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GMCSF derivatives, or combinations thereof. The use of one or more agents to coat the top surface of the needles or micro-needles can provide a burst of agent in the interior of the blood vessel and/or the blood vessel itself during and/or after insertion of the stent, graft, and/or other suitable device.

Figure 14:
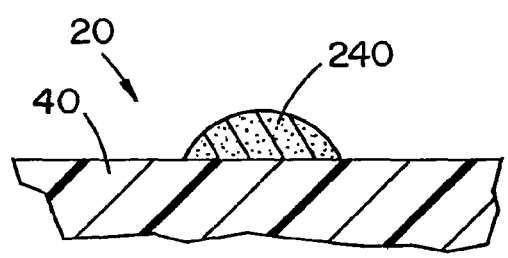
FIG. 14 is a cross-sectional view along line 3-3 of FIG. 2 illustrating a biodegradable material that forms a device that includes one or more micro-structures on the surface of the device which are formed of one or more polymers and agents.

Referring now to FIG. 14, the biodegradable material 40 of stent, graft, and/or other suitable device 20 includes one or more surface structures or micro-structures 140 in the form of a mound; however, it can be appreciated that other or additional shapes can be used. The mound is formed on the surface of the stent, graft, and/or other suitable device. The mound can be formed by MEMS technology and/or by other processes. The mound is shown to be formed of one or more agents; however, it can be appreciated that the mound can be formed of one or more polymers or a combination of one or more polymers and agents. As can also be appreciated, other or additional materials can be used to at least partially form the mound. The one or more agents can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GMCSF derivatives, or combinations thereof; however other or additional agents can be used. The one or more agents used to form the mound can provide a burst of agent in the interior of a body passageway and/or the body passageway itself during and/or after insertion of the stent, graft, and/or other suitable device in the body passageway; however, this is not required. As can be appreciated, a layer of one or more polymers can be coated on the mound; however, this is not required. The polymer layer can be used to control the release rate of the one or more agents from the mound; however, this is not required. The polymer layer can also or alternatively provide protection to the mound structure; however, this is not required. When the mound includes and/or is coated with one or more polymers, such polymers can include, but are not limited to, parylene, parylene C, parylene N, parylene F, PLGA, PEVA, PLA, PBMA, POE, PGA, PLLA, PAA, PEG, chitosan and/or derivatives of one or more of these polymers.

Figure 15:
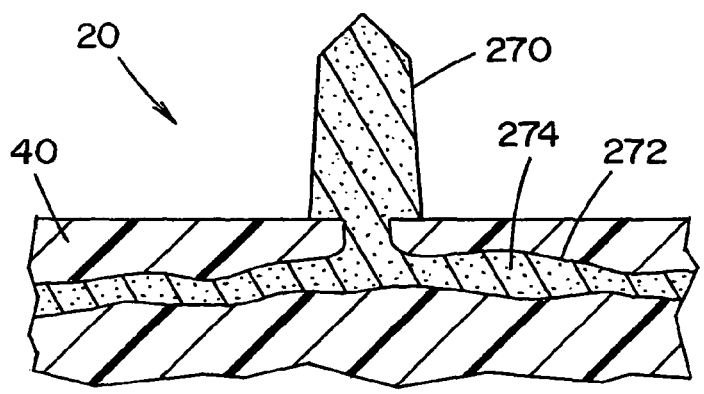
FIG. 15 is a cross-sectional view along line 3-3 of FIG. 2 illustrating a biodegradable material that forms a device that includes a plurality of another type of micro-needles on the surface of the biodegradable material which are formed of one or more agents and which are interconnected to at least internal channel in the biodegradable material which is filled with one or more agents.
Figure 16:
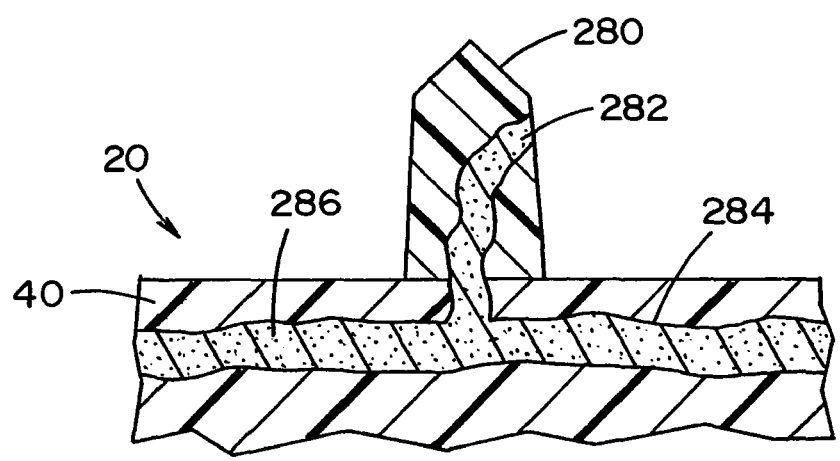
FIG. 16 is a cross-sectional view along line 3-3 of FIG. 2 illustrating a biodegradable material that forms a device that includes a plurality of another type of micro-needles on the surface of the biodegradable material which are formed of one or more polymers and which the micro-needles include a channel filled with one or more agents and which channel in the micro-needle is interconnected to at least an internal channel in the biodegradable material which is filled with one or more agents.
Figure 18:
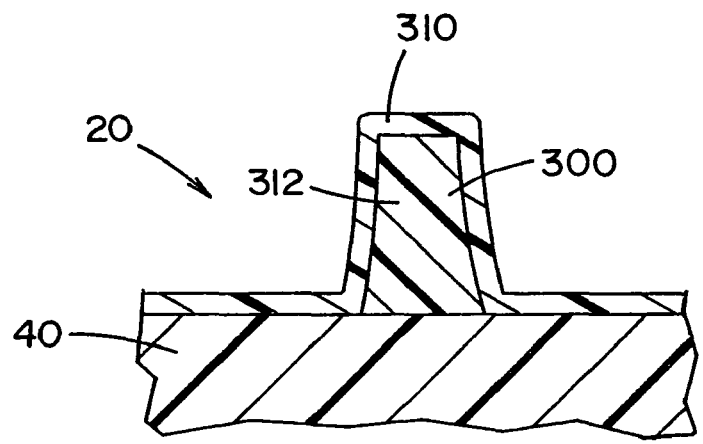
FIG. 18, is a cross-sectional view along line 3-3 of FIG. 2 illustrating one or more micro-needles on the surface of the device which one or more micro-needles are formed from one or more polymers and/or agents and are coated with one or more polymers and/or agents.

Referring now to FIGS. 15, 16 and 18, the biodegradable material 40 of stent, graft, and/or other suitable device 20 includes one or more needles or micro-needles 150, 200, 300. These needles or micro-needles can be formed by MEMS technology and/or by other processes. The one or more needles or micro-needles are formed on the surface of the stent, graft, and/or other suitable device. The one or more needles or micro-needles can formed from one or more agents, polymers, and/or adhesives. The polymer can be porous, non-porous, biodegradable and/or biostable. Polymers that can be used to at least partially form the one or more needles or micro-needles include, but are not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. Non-limiting examples of one or more agents that can be used can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof; however other or additional agents can be used.

Referring to FIG. 15, the one or more needles or micro-needles 150 are formed from one or more agents. As can be appreciated, a layer of one or more polymers can be coated on the one or more needles or micro-needles, not shown; however, this is not required. The polymer layer can be used to control the release rate of the one or more agents from the one or more needles or micro-needles; however, this is not required. The polymer layer can also or alternatively provide protection to the structure of the one or more needles or microneedles; however, this is not required. When the one or more needles or micro-needles includes and/or is coated with one or more polymers, such polymers can include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof. As illustrated in FIG. 14, the needle or microneedle is formed over an opening in the surface of the biodegradable material which opening is connected to a surface structure and/or micro-structure 160 in the biodegradable material. The surface structure and/or micro-structure is shown to be a channel; however, other or additional surface structures and/or micro-structures can be included in the biodegradable material. These surface structures and/or micro-structures can be formed by MEMS technology and/or by other processes. The surface structure and/or micro-structure 160 is shown to be filled with one or more agents 170; however, it can be appreciated that the surface structures and/or micro-structures can include other or additional materials (e.g., polymers, adhesive, etc.); however, this is not required. As can also be appreciated, the surface structures and/or micro-structures can be partially or fully empty of any type of material; however, this is not required. The one or more agents 170 in the surface structure and/or micro-structure 160 can be the same or different from the one or more agents that at least partially form the one or more needles or micro-needles 150.

Referring now to FIG. 16, the biodegradable material 40 of stent, graft, and/or other suitable device 20 includes one or more needles or micro-needles 200. These needles or micro-needles can be formed by MEMS technology and/or by other processes. The one or more needles or micro-needles are formed on the surface of the stent, graft, and/or other suitable device. The one or more needles or micro-needles are formed from one or more polymer. As can be appreciated, the one or more needles or microneedles can also or alternatively be formed from one or more agents and/or adhesives. The polymer can be porous, non-porous, biodegradable and/or biostable. Polymers that can be used to at least partially form the one or more needles or micro-needles include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof; however, other or additional polymers can be used. The one or more needles or micro-needles are shown to include a channel that is filled with one or more agents. As can be appreciated, other or additional materials can be included in the channel in the one or more needles or micro-needles (e.g., polymer, adhesive, etc.). As can be appreciated, a layer of one or more polymers can be coated on the one or more needles or micro-needles; however, this is not required. The polymer layer can be used to control the release rate of the one or more agents from the one or more needles or micro-needles; however, this is not required. The polymer layer can also or alternatively provide protection to the structure of the one or more needles or micro-needles; however, this is not required. When the one or more needles or micro-needles include and/or are coated with one or more polymers, such polymers can include, but are not limited to, parylene, a parylene derivative, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, or combinations thereof. The surface of the one or more needles or microneedles can include a layer of one or more agents to provide a burst of biological agent in the interior of the body passageway and/or the body passageway itself during and/or after insertion of the stent, graft, and/or other suitable device; however, this is not required. The one or more agents that can be used can include, but are not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GMCSF derivatives, or combinations thereof; however other or additional agents can be used. The channel of one or more agents 210 in the one or more needles or microneedles 200 are shown to be connected to an opening in the surface of the biodegradable material which opening is connected to a surface structure and/or micro-structure 220 in the biodegradable material. The surface structure and/or micro-structure is shown to be a channel; however, other or additional surface structures and/or micro-structures can be included in the biodegradable material. These surface structures and/or micro-structures can be formed by MEMS technology and/or by other processes. The surface structure and/or micro-structure 220 is shown to be filled with one or more agents 230; however, it can be appreciated that the surface structure and/or micro-structures can include other or additional materials (e.g., polymers, adhesive, etc.); however, this is not required. As can also be appreciated, the surface structure and/or micro-structures can be partially or fully empty of any type of material; however, this is not required. The one or more agents 230 in the surface structure and/or micro-structure 220 can be the same or different from the one or more agents 210 in the channel of the one or more needles or micro-needles 200.

Referring now to FIG. 18, one or more needles or micro-needles 300 on biodegradable material 40 of stent, graft, and/or other suitable device 20 are formed from one or more polymers 312. As can be appreciated, the one or more needles or micro-needles can also or alternatively be formed from one or more agents and/or adhesives. The polymer can be porous, non-porous, biodegradable and/or biostable. Polymers that can be used to at least partially form the one or more needles or micro-needles include, but are not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. One or more polymer layers 310 are coated on the top of the one or more needles or microneedles. As can be appreciated, layer 310 can also or alternatively be formed from one or more agents and/or adhesives. The one or more polymer layers 310 can include one or more polymers. Layer 310 can include one or more porous polymer and/or non-porous polymers. Layer 310 can include one or more biostable and/or biodegradable polymers. The one or more polymers can include, but are not limited to, parylene, parylene C, parylene N, parylene F, PLGA, PEVA, PLA, PBMA, POE, PGA, PLLA, PAA, PEG, chitosan and/or derivatives of one or more of these polymers; however, other or additional polymers can be used. The one or more polymers that form the layer 310 can be the same or different from the one or more polymers that form the one or more needles or micro-needles 300. Layer 310 can be used to 1) provide protection to the structure of the one or more needles or micro-needles 300, 2) at least partially control a rate of degradation of the one or more needles or micro-needles 300, and/or 3) at least partially control a rate of release of one or more agents on and/or in the one or more needles or micro-needles 300. As can be appreciated, layer 310 can have other or additional functions. The surface of the layer 310 can be or include one or more layers of one or more agents to provide a burst of agent in the interior of a body passageway and/or in the body passageway itself during and/or after insertion of the stent, graft, and/or other suitable device; however, this is not required. The one or more agents that can be used can include, but are not limited to, trapidil, trapidil derivatives, 5-Phenylmethimazole, 5-Phenylmethimazole derivatives, GM-CSF, GM-CSF derivatives, or combinations thereof; however other or additional agents can be used.

Figure 19:
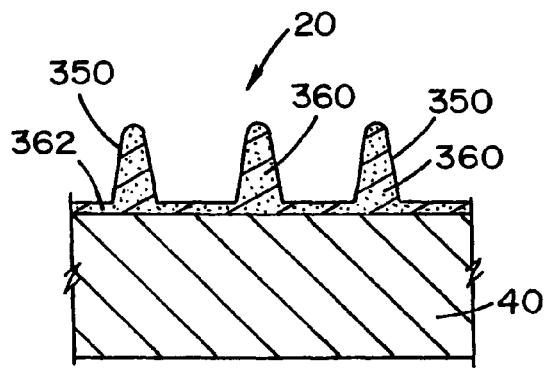
FIG. 19 is a cross-sectional view along line 3-3 of FIG. 2 illustrating microneedles on the surface of the device that are formed of a agent.

Referring now to FIG. 19, the base structure 40 of stent, graft, and/or other suitable device 20 includes one or more needles or micro-needles 350. The one or more needles or micro-needles are formed on the surface of the base structure. The one or more needles or micro-needles are formed from one or more agents and/or one or more polymer 360. A layer 362 of agent and/or polymer is also formed on the surface of the base structure. In one non-limiting example, the one or more needles or micro-needles 350 are formed from one or more agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In this non-limiting example, layer 362 is also formed from one or more agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, combinations thereof. As can be appreciated, the one or more agents in layer 362 and forming the one or more needles or micro-needles 350 can be the same or different. The use of one or more agents to coat the top surface of the base structure and/or to form one or more needles or micro-needles can provide a burst of one or more agent in the treatment area (e.g., body passageway, etc.) after insertion of the stent, graft, and/or other suitable device. In another non-limiting example, the one or more needles or micro-needles 350 are formed from one or more agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In this non-limiting example, layer 362 is formed from one or more polymers. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers are non-porous polymers, the one or more nonporous polymers can include, but are not limited to, parylene C, parylene N, parylene F and/or a parylene derivative. The use of one or more agents to form one or more needles or micro-needles can provide a burst of one or more agent in the treatment area (e.g., body passageway, etc.) after insertion of the stent, graft, and/or other suitable device. In still another non-limiting example, the one or more needles or micro-needles 350 are formed from one or more polymers. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers are non-porous polymers, the one or more non-porous polymers can include, but are not limited to, parylene C, parylene N, parylene F and/or a parylene derivative. In this non-limiting example, layer 362 is formed from one or more agents that include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The use of one or more agents to form layer 362 can provide a burst of one or more agent in the treatment area (e.g., body passageway, etc.) after insertion of the stent, graft, and/or other suitable device; however, this is not required.

Figure 20:
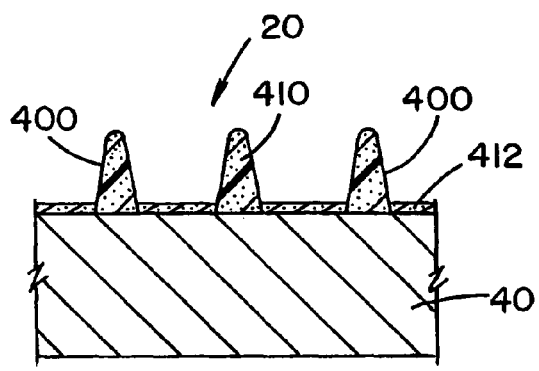
FIG. 20 is a cross-sectional view along line 3-3 of FIG. 2 illustrating microneedles on the surface of the device that are formed of a agent and polymer.

Referring now to FIG. 20, the base structure 40 of stent, graft, and/or other suitable device 20 includes one or more needles or micro-needles 400. The one or more needles or micro-needles are formed on the surface of the base structure. The one or more needles or micro-needles are formed from one or more agents and one or more polymers 410. A layer 412 of agent and/or polymer is also formed on the surface of the base structure. As can be appreciated, the composition of layer 412 and forming the composition of the one or more needles or microneedles 400 can be the same or different. In one non-limiting example, the one or more agents that at least partially form layer 412 and/or the one or more needles or microneedles 400 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that at least partially form layer 412 and/or the one or more needles or micro-needles 400 can include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that at least partially form layer 412 and/or the one or more needles or microneedles 400 include a non-porous polymer to at least partially control a rate of release by molecular diffusion of the one or more agents that are mixed with the polymer. The inclusion of one or more agents in the one or more needles or micro-needles can provide controlled release of agent in the treatment area (e.g., body passageway, etc.) after insertion of the stent, graft, and/or other suitable device; however, this is not required. The use of one or more biological agents to form layer 412 and/or one or more needles or micro-needles 400 can provide a burst of one or more agent in the treatment area (e.g., body passageway, etc.) after insertion of the stent, graft, and/or other suitable device; however, this is not required.

Figure 21:
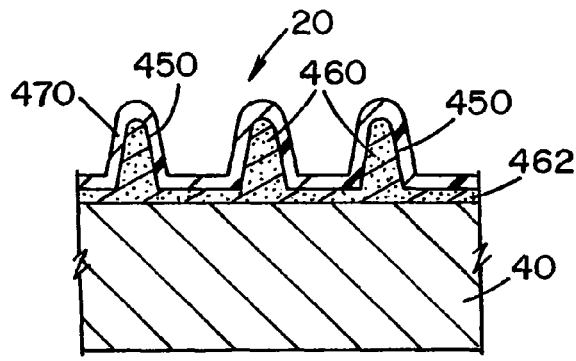
FIG. 21 is a cross-sectional view along line 3-3 of FIG. 2 illustrating microneedles on the surface of the device that are formed of a agent and coated with a polymer.

Referring now to FIG. 21, FIG. 21 is a modification of the arrangement illustrated in FIG. 19. In FIG. 21, a coating 470, that is formed of one or more polymers and/or agents is placed over one or more needles or micro-needles 450 and layer 462. Specifically, the base structure 40 of stent, graft, and/or other suitable device 20 includes one or more needles or micro-needles 450. The one or more needles or micro-needles are formed on the surface of the base structure. The one or more needles or micro-needles are formed from one or more agents and/or polymers 460. A layer 462 of agent and/or polymer is also formed on the surface of the base structure. The composition of layer 462 and one or more needles or micro-needles can be the same or different. In one non-limiting example, the one or more agents that can at least partially form layer 463 and/or one or more needles or micro-needles 450 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that can at least partially form layer 463 and/or one or more needles or micro-needles include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 463 and/or one or more needles or micro-needles 450 include one or more non-porous polymer such as, but not limited to, parylene C, parylene N, parylene F and/or a parylene derivative. The one or more non-porous polymers can be used to at least partially control a rate of release by molecular diffusion of the one or more agents in layer 463 and/or in the one or more needles or micro-needles 450; however, this is not required. Layer 470 that is coated on the top of the one or more needles or micro-needles and layer 462 includes one or more agents and/or polymers. In one non-limiting example, the one or more agents that can at least partially form layer 470 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In one non-limiting example, the one or more polymers that can at least partially form layer 470 include one or more porous and/or non-porous polymers, and/or one or more biostable and/or biodegradable polymers. Nonlimiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers include one or more non-porous polymers, such non-porous polymer can include, but is not limited to, parylene C, parylene N, parylene F and/or a parylene derivative. The one or more non-porous polymers can be used to at least partially control a rate of release by molecular diffusion of the one or more agents in layer 463, layer 470 and/or in the one or more needles or micro-needles 450; however, this is not required. When one or more agents at least partially form layer 470 and/or are coated on layer 470, not shown, the one or more agents can provide a burst of one or more agent in the treatment area (e.g., body passageway, etc.) after insertion of the stent, graft, and/or other suitable device; however, this is not required.

Figure 22:
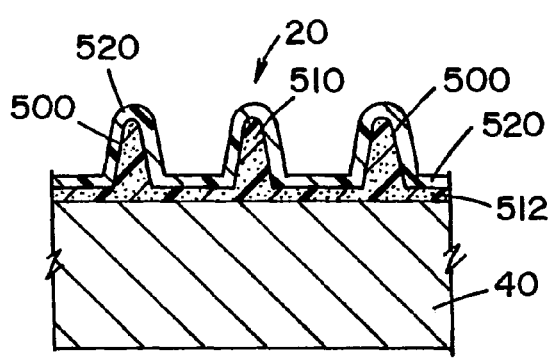
FIG. 22 is a cross-sectional view along line 3-3 of FIG. 2 illustrating microneedles on the surface of the device that are formed of a agent and polymer and coated with a polymer.

Referring now to FIG. 22, FIG. 22 is a modification of the arrangement illustrated in FIG. 20. In FIG. 22, a coating 520, that is formed of one or more polymers and/or agents is placed over one or more needles or micro-needles 500 and layer 512. The composition of layer 520 and layer 512 and/or one or more needles or micro-needles can be the same or different. Specifically, the base structure 40 of stent, graft, and/or other suitable device 20 includes one or more needles or micro-needles 500. The one or more needles or micro-needles are formed on the surface of the base structure. The one or more needles or micro-needles are formed from a mixture of one or more agents and one or more polymers 510. A layer 512 of agent and polymer is also formed on the surface of the base structure. As can be appreciated, layer 512 and/or one or more needles or micro-needles 500 can be formed only of one or more polymers or one or more agents. The composition of layer 512 and one or more needles or micro-needles 500 can be the same or different. In one non-limiting example, the one or more agents that can at least partially form layer 512 and/or one or more needles or micro-needles 500 include trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that can at least partially form layer 512 and/or one or more needles or micro-needles 500 include one or more porous polymers and/or non-porous polymers, and/or one or more biostable and/or biodegradable polymers. Nonlimiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 512 and/or one or more needles or micro-needles 500 include one or more non-porous polymers such as, but not limited to, parylene C, parylene N, parylene F and/or a parylene derivative. The one or more non-porous polymers can be used to at least partially control a rate of release by molecular diffusion of the one or more agents in layer 512 and/or in the one or more needles or micro-needles 500; however, this is not required. In one non-limiting example, the one or more polymers that can at least partially form layer 520 include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers include one or more non-porous polymers, such non-porous polymer can include, but not limited to, parylene C, parylene N, parylene F and/or a parylene derivative. The one or more non-porous polymers can be used to at least partially control a rate of release by molecular diffusion of the one or more agents in layer 512, layer 520 and/or in the one or more needles or micro-needles 500; however, this is not required. When one or more agents at least partially form layer 520 and/or are coated on layer 520, not shown, the one or more agents can provide a burst of one or more agent in the treatment area (e.g., body passageway, etc.) after insertion of the stent, graft, and/or other suitable device; however, this is not required.

Figure 23:
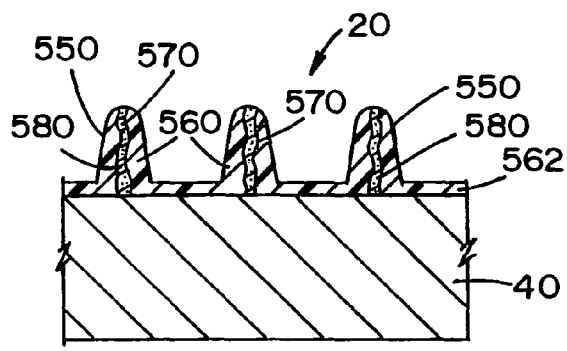
FIG. 23 is a cross-sectional view along line 3-3 of FIG. 2 illustrating microneedles on the surface of the device that are formed of a polymer and includes an internal cavity that includes a agent; and, FIG. 24 is a cross-sectional view of a micro-needle on a that is penetrating into the inner surface of a body passageway or organ.

Referring now to FIG. 23, FIG. 23 is another modification of the arrangement illustrated in FIG. 20. In FIG. 23, one or more internal channels 570 are formed in one or more needles or micro-needles 550. The one or more internal channels 570 can include one or more agent and/or polymers. Specifically, the base structure 40 of stent, graft, and/or other suitable device 20 includes one or more needles or micro-needles 550. The one or more needles or micro-needles are formed on the surface of the base structure. The one or more needles or micro-needles are formed from one or more polymers and/or agents 560. A layer 562 of polymer and/or agent is also formed on the surface of the base structure. The composition of layer 562 and one or more needles or micro-needles can be the same or different. The one or more polymers that can at least partially form layer 562 and/or one or more needles or micro-needles 550 include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 562 and/or one or more needles or micro-needles 550 include one or more non-porous polymers such as, but not limited to, parylene C, parylene N, parylene F and/or a parylene derivative. The one or more non-porous polymers can be used to at least partially control a rate of release by molecular diffusion of the one or more agents in layer 562, in the one or more needles or micro-needles 550, and/or in one or more internal channels 570; however, this is not required. One or more of the needles or micro-needles 550 include an internal channel 570. The internal channel is illustrated as including one or more biological agents 580; however, it can be appreciated that one or more channels can include a mixture of one or more polymers and/or agents, or only one or more polymers. In one nonlimiting example, the one or more agents includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The top opening of the channel enables delivery of one or more agents directly into treatment area (e.g., a wall of a body passageway or organ, etc.). The one or agents in internal channel 570 can pass through and/or molecularly diffuse through the one or more polymers that at least partially form the one or more needles or micro-needles; however, this is not required. The release of the one or more agents through the one or more polymers that at least partially form the one or more needles or micro-needles can be a controlled or an uncontrolled release rate. As can be appreciated, a layer of agent, not shown, can be coated one or more needles or micro-needles 550. The layer of agent could include one or more agents. The placement of the layer of agent on the one or more needles or micro-needles 550 can provide a burst of one or more agents in the treatment area; however, this is not required. As can be appreciated, other combinations of polymer layer and/or layer of biological agent can be used on the stent, graft, and/or other suitable device. As can also or alternatively be appreciated, a layer of polymer, not shown, can be coated one or more needles or micro-needles 550. The layer of polymer could include one or more polymers. The placement of the layer of polymer on the one or more needles or micro-needles 550 can be used to a) at least partially control a release rate of one or more agents from the stent, graft, and/or other suitable device, and/or 2) provide structural support and/or protection to one or more needles or micro-needles. As can be appreciated, the polymer layer, when used, can have other or additional functions. These other combinations are also encompassed within the scope of the present invention.

Figure 24:
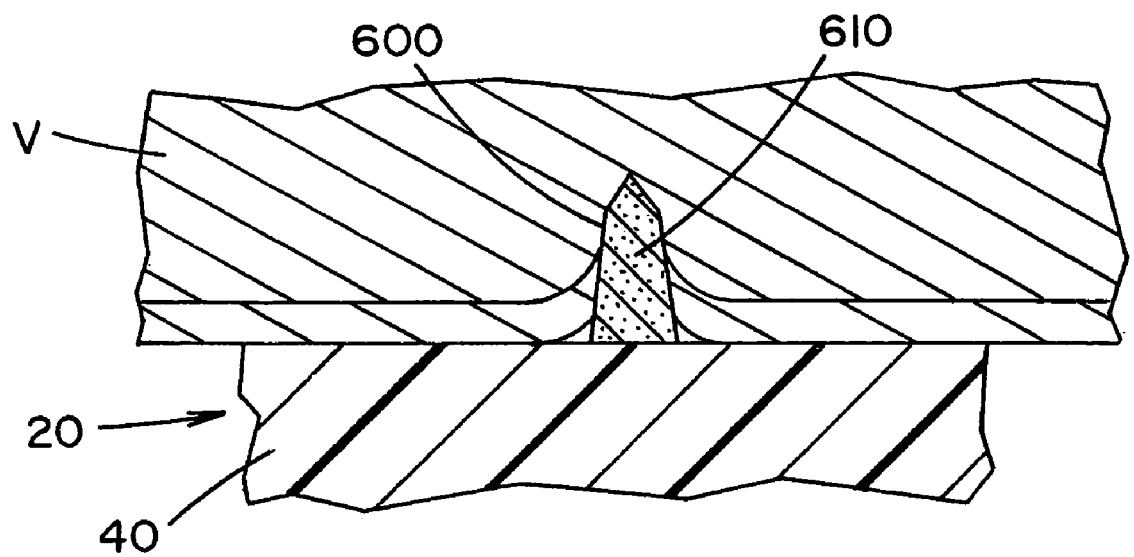

Referring now to FIG. 24, there is illustrated an enlarged portion of a surface of a stent, graft, and/or other suitable device 20 which includes a surface needle, micro-needle or other type of structure or microstructure 600. The needle is shown to include at least one agent 610; however, the needle can also or alternatively include one or more polymers, adhesives, etc. The stent, graft, and/or other suitable device, when in the form of a stent, graft, and/or other suitable device, is illustrated as being in an expanded state. When the stent, graft, and/or other suitable device is inserted or expanded in a treatment area, the needle 600 on the outer surface of the stent, graft, and/or other suitable device engages and/or at least partially penetrates into blood vessel or organ V. When the needle includes one or more agents, the one or more agents are at least partially locally applied to a treatment area. This can be a significant advantage over system wide treatment with one or more agents. The locally treatment with one or more agent via the needle can more effectively and/or efficiently direct the desired agents to a treated area. The release of one or more agents from the needle can be controlled, if desired, to direct the desired amount of one or more agents to a treated area over a desired period of time. When the stent, graft, and/or other suitable device is expanded in a blood vessel, the one or more needles enable local delivery of one or more agents into the wall of the blood vessel. This local delivery is especially advantageous in large and/or thick blood vessels wherein system wide drug treatment is not very effective. In addition, the local delivery of agent by the needle directly into the blood vessel can be more effective than only releasing the agent from the surface of the stent, graft, and/or other suitable device since diffusion from the surface of the stent, graft, and/or other suitable device to the larger and/or thicker blood vessel may not be as effective as direct delivery by the needles to the blood vessel. The one or more needles on the stent, graft, and/or other suitable device surface can also or alternatively be used to facilitate in securing the stent, graft, and/or other suitable device to the treatment area during the expansion and/or insertion of the stent, graft, and/or other suitable device in a treatment area. The various embodiment of the device set forth above represent a significant advancement over the current state of the art. The device includes or is formed of a biodegradable material. The biodegradable properties of one or more portions of the medical device enable the device to at least partially dissolve and/or be bodily absorbed after insertion in a patient. This feature is significant wherein the device is subject to repeated bending that can result in fracturing, micro-fracturing and/or braking of the medical device over time. The biodegradability of one or more portions of the device enables one or more portions of the damaged device to be remove without use of evasive surgical techniques. The biodegradability of the one or more portions of the device can also or alternatively enable the device to functions as a agent delivery device that deliveries one or more agents locally and/or systemically in a controlled or uncontrolled manner. The device when in the form of stent, graft, and/or other suitable device can be used to passivate vulnerable plaque in a body passageway. For instance, the device in the form of a stent, graft, and/or other suitable device can be designed so that a reduce amount of radial force is exerted in a body passageway after the stent, graft, and/or other suitable device has been expanded. The reduced amount of radial force applied by the stent, graft, and/or other suitable device can reduce the amount of vulnerable plaque that become dislodged from the body passageway. The dislodgement of plaque can result in blockage of the body passageway upstream from the inserted stent, graft, and/or other suitable device. The stent, graft, and/or other suitable device is maintained in place in the body passageway by frictional content between the wall of the body passageway and the expanded stent, graft, and/or other suitable device. The one or more biological agents coated on and/or contained in the stent, graft, and/or other suitable device can be selected to slowly remove the plaque from the treated area. As can be appreciated, the one or more polymers on the device can be naturally biodegradable or become biodegradable or more biodegradable upon a certain event (e.g., exposure to electromagnetic radiation, etc.). Likewise, the one or more agents can be naturally active or be activated upon a certain event (e.g., exposure to electromagnetic radiation, etc.). Furthermore, the one or more agents can be naturally soluble or become soluble upon a certain event (e.g., exposure to electromagnetic radiation, etc.).

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall there between.

We claim:

1. An expandable medical device for insertion in a body passageway that is used in treating dissected blood vessels, vascular malformations, vulnerable plaque by encapsulation, vulnerable plaque by passivation, nerve dissection of the central nervous system, incompetent valves, pulmonary embolism, narrowing of a body passageway, and combinations thereof, said expandable medical device including a body having an unexpanded and expanded cross-section area and a biological agent coated or impregnated on an other surface of said body, majority of said body is formed of a biodegradable polymer system designed to degrade when exposed to fluids in the body passageway so that at least a portion of said body degrades over time and removes itself from a treatment site in said body passageway, a portion of an outer surface of said medical device including a plurality of microstructures that extend upwardly from and above said outer surface of said body, said plurality of microstructures at least partially formed of said biological agent, said plurality of microstructures having a shape and size that is designed to penetrate into said body passageway at the treatment site when said body is expanded to said expanded cross-sectional area and to deliver said biological agent in said penetrated region of said body passageway, said plurality of microstructures having a height of less than 1000 microns.

2. The expandable medical device as defined in claim 1, wherein said body is in the form of a stent.

3. The expandable medical device as defined in claim 2, wherein said body is formed of about 100 percent biodegradable material.

4. The expandable medical device as defined in claim 3, wherein said outer surface of said body including a body coating, said plurality of microstructures extending upwardly from said body coating, said body coating including biodegradable polymer, biological agent, and combinations thereof, said body coating having a different composition from said biodegradable polymer system of said body, said body coating having a thickness of at least about 0.01 μm to less than about less than about 150 μm.

5. The expandable medical device as defined in claim 1, wherein said body is formed of about 100 percent biodegradable material.

6. The expandable medical device as defined in claim 1, wherein said outer surface of said body including a body coating, said plurality of microstructures extending upwardly from said body coating, said body coating including biodegradable polymer, biological agent, and combinations thereof, said body coating having a different composition from said biodegradable polymer system of said body, said body coating having a thickness of at least about 0.01 μm to less than about less than about 150 μm.

7. The expandable medical device as defined in claim 6, including a protective outer polymer coating on said body coating, said protective outer polymer coating including a) one or more polymers selected from the group consisting of parylene, PLGA, PEVA, PBMA, PLA, POE, PGA, PLLA, PAA, PEG and chitosan, b) one or more derivatives of polymers selected from the group consisting of parylene, PLGA, PEVA, PBMA, PLA, POE, PGA, PLLA, PAA, PEG and chitosan, or c) a combination of a) and b).

8. The expandable medical device as defined in claim 6, wherein said protective outer polymer coating controls a rate of degradation of said biodegradable polymer on said body.

9. The expandable medical device as defined in claim 1, including a protective outer polymer coating on said plurality of microstructures, said protective outer polymer coating including a biodegradable polymer, said protective coating designed to inhibit or prevent damage to said plurality of microstructures as said body is inserted into said body passageway and to said treatment site, said protective outer polymer coating having a thickness of less than about 300 μm.

10. The expandable medical device as defined in claim 4, including a protective outer polymer coating on said plurality of microstructures, said protective outer polymer coating including a biodegradable polymer, said protective coating designed to inhibit or prevent damage to said plurality of microstructures as said body is inserted into said body passageway and to said treatment site, said protective outer polymer coating having a thickness of less than about 300 µm.

11. The expandable medical device as defined in claim 10, including a protective outer polymer coating on said body coating, said protective outer polymer coating including a) one or more polymers selected from the group consisting of parylene, PLGA, PEVA, PBMA, PLA, POE, PGA, PLLA, PAA, PEG and chitosan, b) one or more derivatives of polymers selected from the group consisting of parylene, PLGA, PEVA, PBMA, PLA, POE, PGA, PLLA, PAA, PEG and chitosan, or c) a combination of a) and b).

12. The expandable medical device as defined in claim 11, wherein said protective outer polymer coating controls a rate of degradation of said biodegradable polymer on said body.

13. The expandable medical device as defined in claim 12, wherein said agent ranging from about 0.01-100 ug per mm$^2$, said agent at least about 0.01 weight percent of the device, and combinations thereof.

14. The expandable medical device as defined in claim 13, wherein said biological agent is used to promote the growth of an integral endothelial layer.

15. The expandable medical device as defined in claim 14, wherein said biological agent includes a) one or more agents selected from the group consisting of trapidil, taxol, cytochalasin, paclitaxel, rapamycin, and GM-CSF, b) one or more agents selected from the group consisting of trapidil derivative, taxol derivative, cytochalasin derivative, paclitaxel derivative, rapamycin derivative, and GM-CSF derivative, or c) a combination of a) and b).

16. The expandable medical device as defined in claim 15, wherein said body includes a plurality of high strain regions when said body is expanded from said unexpanded cross-sectional area and to said expanded cross-sectional area, a plurality of said high strain regions formed of biodegradable material so that such high strain regions degrade at a faster rate as compared to non-high strain regions on said body.

17. The expandable medical device as defined in claim 16, wherein said body contacts a balloon, a sheath, or combination thereof when inserted in to said body passageway, a plurality of said microstructures deigned to increase retention of said body to said balloon, said sheath, or combinations thereof.

18. The expandable medical device as defined in claim 17, wherein said biological agent is incorporated into said body.

19. The expandable medical device defined in claim 1, wherein said agent ranging from about 0.01-100 ug per mm$^2$, said agent at least about 0.01 weight percent of the device, and combinations thereof.

20. The expandable medical device as defined in claim 1, wherein said biological agent is used to promote the growth of an integral endothelial layer.

21. The expandable medical device as defined in claim 1, wherein said biological agent includes a) one or more agents selected from the group consisting of trapidil, taxol, cytochalasin, paclitaxel, rapamycin, and GM-CSF, b) one or more agents selected from the group consisting of trapidil derivative, taxol derivative, cytochalasin derivative, paclitaxel derivative, rapamycin derivative, and GM-CSF derivative, or c) a combination of a) and b).

22. The expandable medical device as defined in claim 1, wherein said body includes a plurality of high strain regions when said body is expanded from said unexpanded cross-sectional area and to said expanded cross-sectional area, a plurality of said high strain regions formed of biodegradable material so that such high strain regions degrade at a faster rate as compared to non-high strain regions on said body.

23. The expandable medical device as defined in claim 1, wherein said body contacts a balloon, a sheath, or combination thereof when inserted in to said body passageway, a plurality of said microstructures deigned to increase retention of said body to said balloon, said sheath, or combinations thereof.

24. The expandable medical device as defined in claim 1, wherein said biological agent is incorporated into said body.

25. The expandable medical device as defined in claim 1, wherein said plurality of biodegradable microstructures extend upwardly from said body having a height of at least about 0.01 µm to less than about 300 µm.

* * * * *